United States Patent
Rosen

(10) Patent No.: US 9,976,169 B2
(45) Date of Patent: May 22, 2018

(54) BIOSENSORS FOR ORGANIC AND INORGANIC ARSENIC

(71) Applicant: THE FLORIDA INTERNATIONAL UNIVERSITY BOARD OF TRUSTEES, Miami, FL (US)

(72) Inventor: Barry P. Rosen, Coral Gables, FL (US)

(73) Assignee: THE FLORIDA INTERNATIONAL UNIVERSITY BOARD OF TRUSTEES, Miami, FL (US)

(*) Notice: Subject to any disclaimer, the term of this patent is extended or adjusted under 35 U.S.C. 154(b) by 327 days.

(21) Appl. No.: 14/413,256

(22) PCT Filed: Jul. 15, 2013

(86) PCT No.: PCT/US2013/050437
§ 371 (c)(1),
(2) Date: Jan. 7, 2015

(87) PCT Pub. No.: WO2014/012089
PCT Pub. Date: Jan. 16, 2014

(65) Prior Publication Data
US 2015/0191762 A1   Jul. 9, 2015

Related U.S. Application Data

(60) Provisional application No. 61/671,167, filed on Jul. 13, 2012.

(51) Int. Cl.
| | | |
|---|---|---|
| *C12N 9/96* | (2006.01) | |
| *C12Q 1/02* | (2006.01) | |
| *C12Q 1/68* | (2018.01) | |
| *C12Q 1/18* | (2006.01) | |
| *G01N 33/84* | (2006.01) | |

(52) U.S. Cl.
CPC .......... *C12Q 1/02* (2013.01); *C12Q 1/18* (2013.01); *C12Q 1/689* (2013.01); *G01N 33/84* (2013.01); *C12Q 2600/142* (2013.01)

(58) Field of Classification Search
None
See application file for complete search history.

(56) References Cited

PUBLICATIONS

Qin et al. (JBC, vol. 282, No. 47, pp. 3446-34355).*
Chen et al. (Environ. Sci. Technol, vol. 4812, pp. 1141-1447.*
Abernathy et al., Health effects and risk assessment of arsenic, J. Nutr., 133(a5 Suppl 1):1536S-8S (2003).
Arao et al., Uptake of aromatic arsenicals from soil contaminated with diphenylarsinic acid by rice, Environ. Sci. Technol., 43(4):1097-101 (2009).
Baumann et al., Analysis of bioavailable arsenic in rice with whole cell living bioreporter bacteria, J. Agric. Food Chem., 55(6):2115-20 (2007).
Bradford, A rapid and sensitive method for the quantitation of microgram quantities of protein utilizing the principle of protein-dye binding, Anal. Biochem., 72:248-54 (1976).
Carlin et al., The ars operon of *Escherichia coli* confers arsenical and antimonial resistance, J. Bacteriol., 177(4):981-6 (1995).
Chang et al., Construction and characterization of amplifiable multicopy DNA cloning vehicles derived from the P15A cryptic miniplasmid, J. Bacteriol., 134(3):1141-56 (1978).
Chen et al., Biosensors for inorganic and organic arsenicals, Biosensors, 4:494-512 (2014).
Chen et al., A novel biosensor selective for organoarsenicals, Appl. Environ. Microbiol., 78(19):7145-7 (2012).
Cortinas et al., Anaerobic biotransformation of roxarsone and related N-substituted phenylarsonic acids, Environ. Sci. Technol., 40(9):2951-7 (2006).
Edmonds et al., Transformations of arsenic in the marine environment, Experientia, 43(5):553-7 (1987).
Environmental Protection Agency, Organic arsenicals: product cancellation order and amendments to terminate uses, Federal Register, 74(188):50187-94 (2009).
Erickson, Field kits fail to provide accurate measure of arsenic in groundwater, Environ. Sci. Technol., 37(1):35A-38A (2003).
Ezeh et al., A sensitive and selective fluorescence sensor for the detection of arsenic(III) in organic media, Inorg. Chem., 51(3):1213-5 (2012).
Gill et al., Calculation of protein extinction coefficients from amino acid sequence data, Anal. Biochem., 182(2):319-26 (1989).
Guzman et al., Tight regulation, modulation, and high-level expression by vectors containing the arabinose PBAD promoter, J. Bacteriol., 177(14):4121-30 (1995).
International Search Report and Written Opinion, International Application No. PCT/US2013/050437, dated Oct. 8, 2013.
Kinniburgh et al., Arsenic contamination in groundwater: some analytical considerations, Talanta, 58(1):165-80 (2002).
Laemmli, Cleavage of structural proteins during the assembly of the head of bacteriophage T4, Nature, 227(5259):680-5 (1970).
Maejima et al., Transformation of diphenylarsinic acid in agricultural soils. J Environ. Qual., 40:76-82 (2011).
Mukhopadhyay et al., Arsenate reductases in prokaryotes and eukaryotes, Environ. Health Perspect., 110 Suppl. 5:745-8 (2002).
Petanen, "Assessment of bioavailable concentrations and toxicity of arsenite and mercury in contaminated soils and sediments by bacterial biosensors", Academic Dissertation, Department of Biosciences, Division of General Microbiology, University of Helsinki, 27 pp. (2001).
Qin et al., Arsenic detoxification and evolution of trimethylarsine gas by a microbial arsenite S-adenosylmethionine methyltransferase, Proc. Natl. Acad. Sci. USA, 103(7):2075-80 (2006).
Qin et al., Biotransformation of arsenic by a Yellowstone thermoacidophilic eukaryotic alga, Proc. Natl. Acad. Sci. USA, 106(13):5213-7 (2009).

(Continued)

*Primary Examiner* — Hope Robinson
(74) *Attorney, Agent, or Firm* — Marshall, Gerstein & Borun LLP

(57) ABSTRACT

Disclosed are methods of detecting organic arsenicals using genetically modified cells.

12 Claims, 19 Drawing Sheets

(56) References Cited

PUBLICATIONS

Qin et al., Convergent evolution of a new arsenic binding site in the ArsR/SmtB family of metalloregulators, J. Biol. Chem., 282(47):34346-55 (2007).

Rahman et al., Effectiveness and reliability of arsenic field testing kits: are the million dollar screening projects effective or not?, Environ. Sci. Technol., 36(24):5385-94 (2002).

Ramanathan et al., Sensing antimonite and arsenite at the subattomole level with genetically engineered bioluminescent bacteria, Anal. Chem., 69(16):3380-4 (1997).

Rensing et al., Heavy metals cycles (arsenic, mercury, selenium, others), pp. 205-219 IN: Schaechter (ed.), Encyclopedia of Microbiology, Elsevier, Oxford, United Kingdom (2009).

Ron, Biosensing environmental pollution, Curr. Opin. Biotechnol., 18(3):252-6 (2007).

San Francisco et al., Identification of the metalloregulatory element of the plasmid-encoded arsenical resistance operon, Nucleic Acids Res., 18(3):619-24 (1990).

Scott et al., Genetically engineered bacteria: electrochemical sensing systems for antimonite and arsenite, Anal. Chem., 69(1):16-20 (1997).

Shetty et al., Luminescence-based whole-cell-sensing systems for cadmium and lead using genetically engineered bacteria, Anal. Bioanal. Chem., 376(1):11-7 (2003).

Shi et al., The role of arsenic-thiol interactions in metalloregulation of the ars operon, J. Biol. Chem., 271(16):9291-7 (1996).

Stolz et al., Biotransformation of 3-nitro-4-hydroxybenzene arsonic acid (roxarsone) and release of inorganic arsenic by Clostridium species, Environ. Sci. Technol., 41(3):818-23 (2007).

Sun et al., Role of cysteinyl residues in sensing Pb(II), Cd(II), and Zn(II) by the plasmid pI258 CadC repressor, J. Biol. Chem., 276(18):14955-60 (2001).

Tchounwou et al., Arsenic toxicity, mutagenesis, and carcinogenesis—a health risk assessment and management approach, Mol. Cell Biochem., 255(1-2):47-55 (2004).

Turdean et al., Design and development of biosensors for teh detection of heavy metal toxicity, Int. J. Electrochemistry, Article ID 343125, 2011:1-15 (2011).

Wu et al., The ArsR protein is a trans-acting regulatory protein, Mol. Microbiol., 5(6):1331-6 (1991).

Xu et al., The chromosomal arsR gene of *Escherichia coli* encodes a trans-acting metalloregulatory protein, J. Biol. Chem., 271(5):2427-32 (1996).

Ye et al., Arsenic biomethylation by photosynthetic organisms, Trends Plant Sci., 17(3):155-62 (2012).

Ye et al., Crystal structure of the *Staphylococcus aureus* pI258 CadC Cd(II)/Pb(II)/Zn(II)-responsive repressor, J. Bacteriol., 187(12):4214-21 (2005).

Yin et al., Biotransformation and volatilization of arsenic by three photosynthetic cyanobacteria, Plant Physiol., 156(3):1631-8 (2011).

Yoshinaga et al., Demethylation of methylarsonic acid by a microbial community, Environ. Microbiol., 13(5):1205-15 (2011).

Zhou et al., *Leishmania* major LmACR2 is a pentavalent antimony reductase that confers sensitivity to the drug Pentostarn, J Biol Chem., 279:37445-51 (2004).

\* cited by examiner

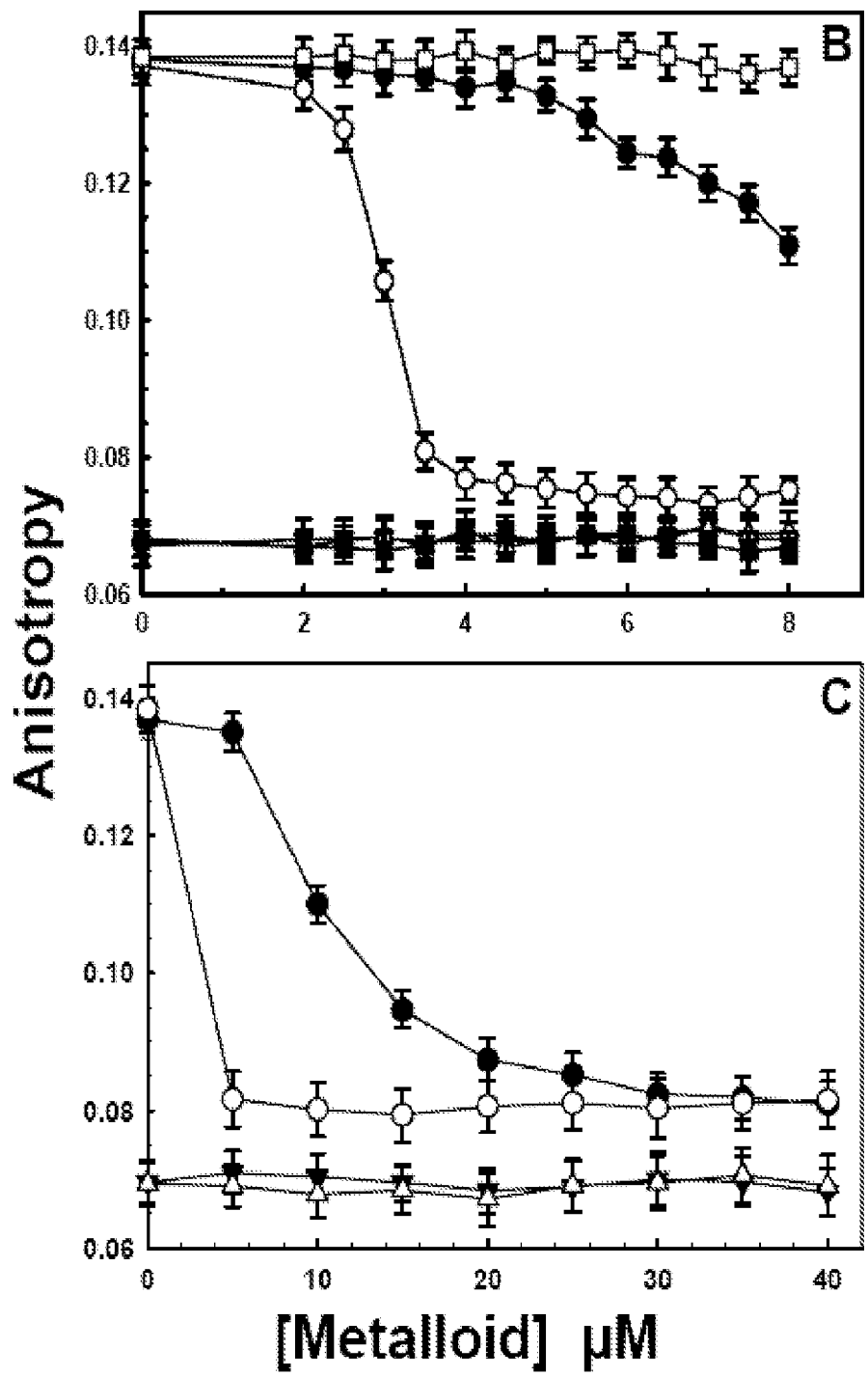
FIGURE 2B,C

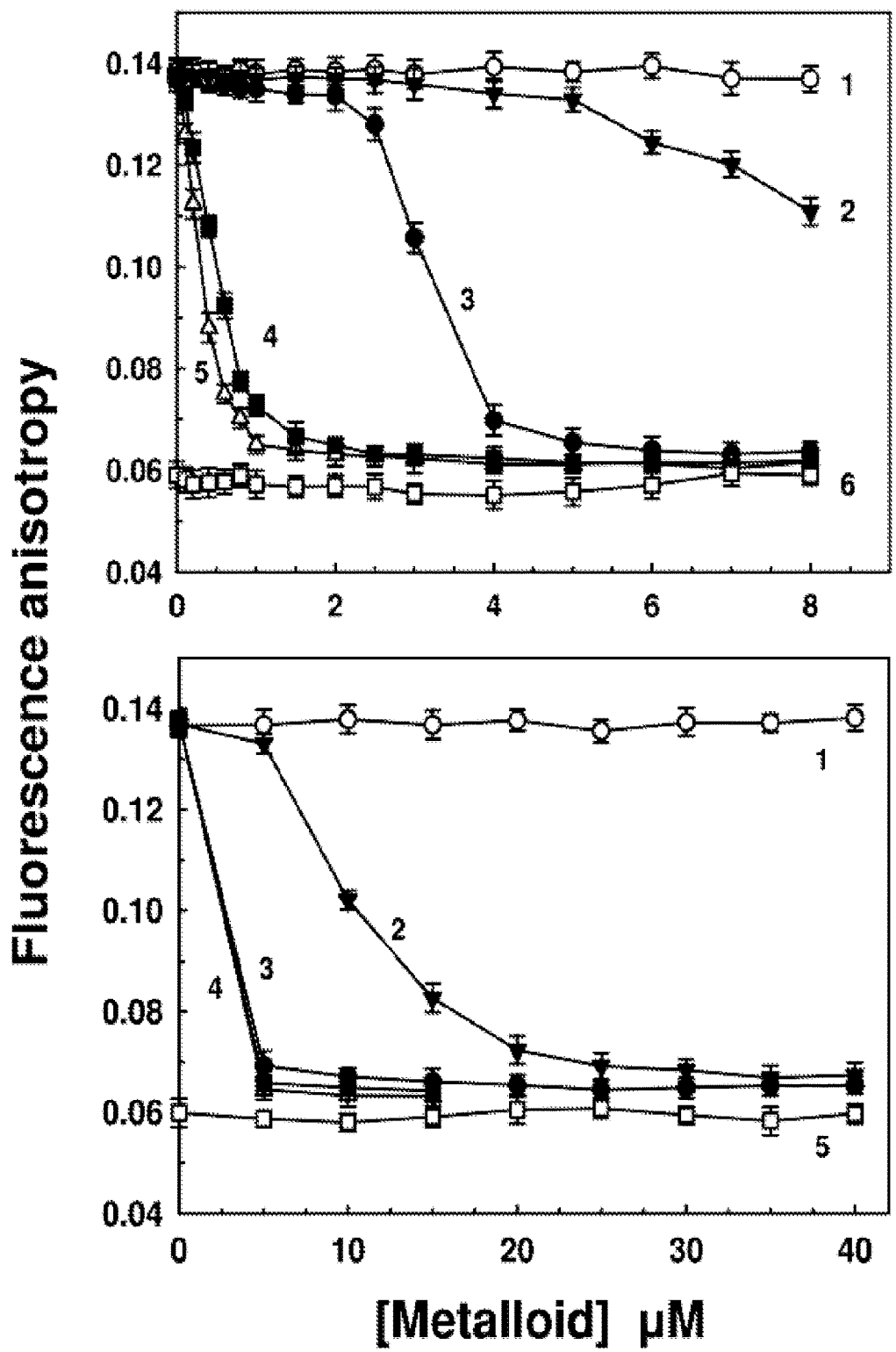
FIGURE 11A,B

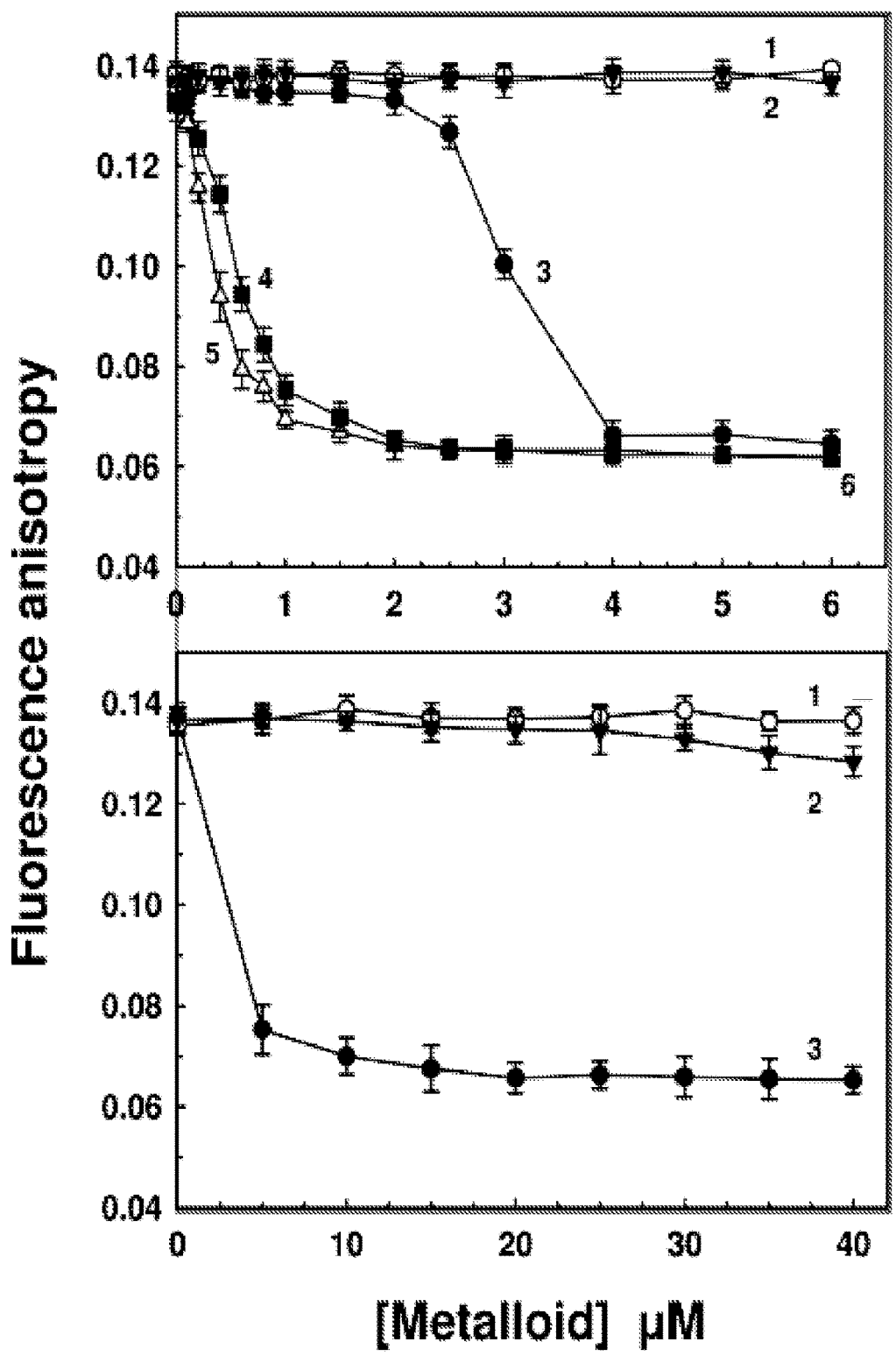
FIGURE 11C,D

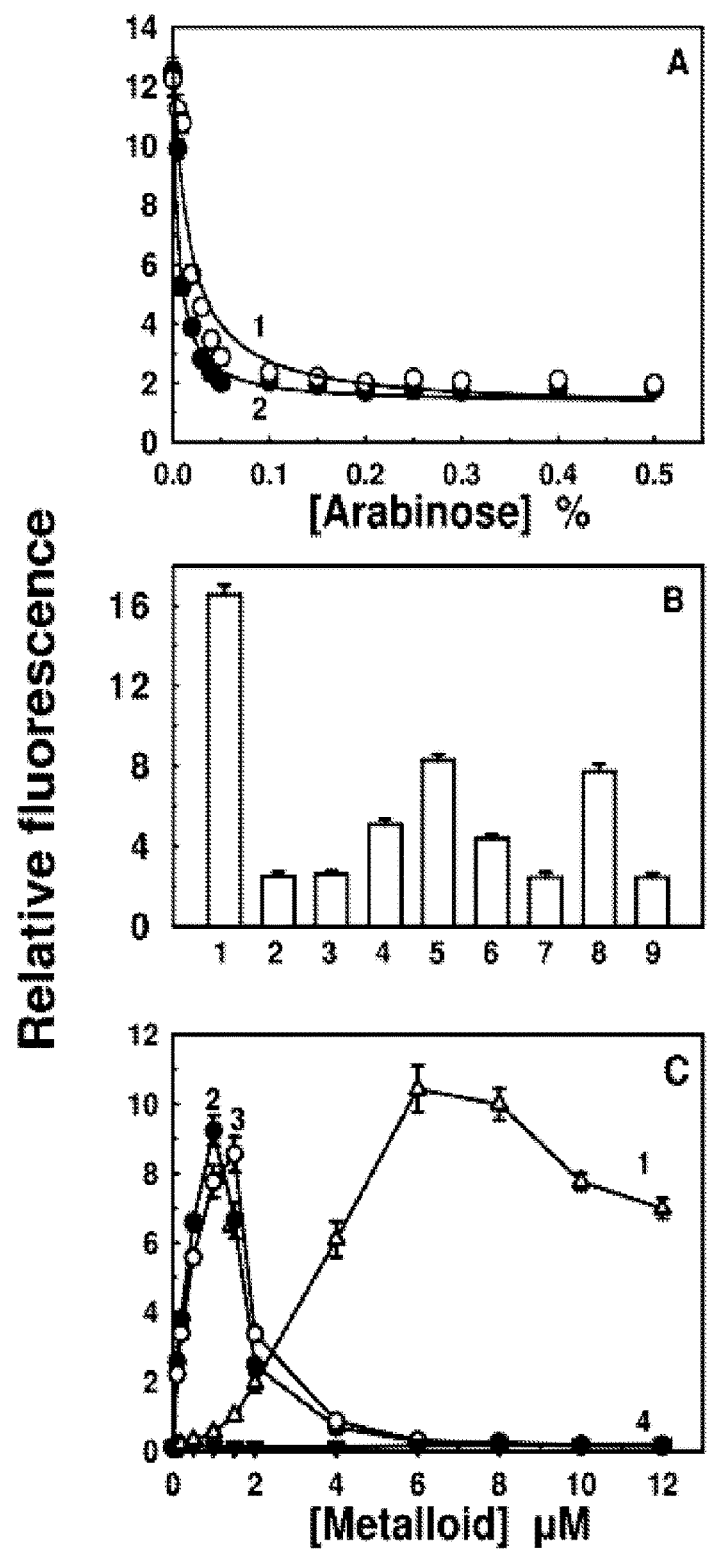
FIGURE 13A,B,C

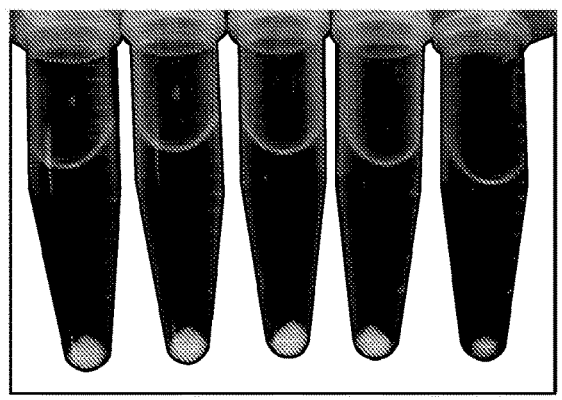
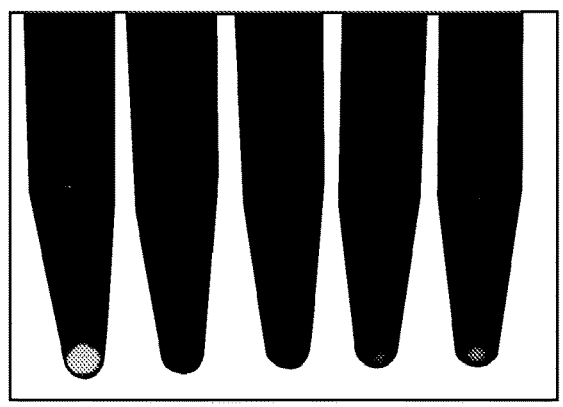
FIGURE 16A
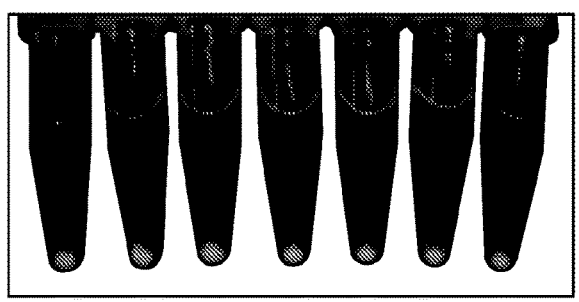
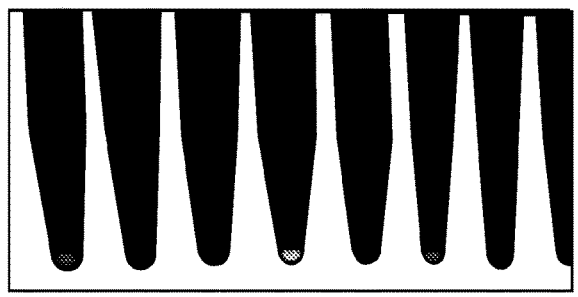
FIGURE 16B

US 9,976,169 B2

BIOSENSORS FOR ORGANIC AND INORGANIC ARSENIC

STATEMENT OF U.S. GOVERNMENT SUPPORT

This invention was made with U.S. government support under Grant No. GM055425, awarded by the National Institutes of Health (NIH). The U.S. Government has certain rights in the invention.

BACKGROUND

Arsenic is a ubiquitous environmental carcinogen that comes from both geochemical and anthropogenic sources. It has been linked to multiple health problems, including skin cancer, bladder cancer, diabetes, as well as cardiovascular and peripheral vascular diseases (1, 30). Consequently, the U.S. Environmental Protection Agency (EPA) ranks arsenic first its Superfund List of Hazardous Substances.

Inorganic arsenic, which is pervasive environmentally from geochemical origins such as volcanoes and hot springs can be either pentavalent (arsenate (As(V)) or trivalent (arsenite (As(III)). Biological activities includes incorporation of arsenic into organic molecules such as arsenobetaine, arsenosugars and arsenolipid, which are found in many marine organisms (8). Arsenic methylation also contributes to the arsenic biogeocycle (21). Microbial methylation, catalyzed by ArsM As(III) S-adenosylmethionine methyltransferases, detoxifies inorganic arsenic, producing a variety of less toxic species including MAs(V) (17, 18, 34, 35). In addition to biogenesis of methylated arsenicals, MAs(V) is also used as an herbicide. Approximately 3,000,000 pounds (1,360,000 kg) of MAs(V) are in commercial use in the USA. Its use has been banned by the EPA after Dec. 31, 2013 except for treatment of cotton because the EPA does not anticipate that arsenic in cotton will end up in the food supply (2). This may be an erroneous assumption since the herbicide can be degraded by microbial activity to MAs(III) and As(III), both of which are more toxic and carcinogenic than MAs(V) (36).

Aromatic arsenicals are also used in animal husbandry to prevent bacterial infections and for growth promotion. For example, derivatives of phenylarsonic acid (PAO) such as 3-nitro-4-hydroxybenzenearsonic acid (roxarsone), p-arsanilic acid, 4-nitrophenylarsonic acid and p-ureidophenylarsonic acid are all used as additives for animal feed. Roxarsone is degraded to 4-hydroxy-3-aminophenylarsonic acid (7) and eventually to inorganic arsenic (28). The related aromatic arsenical diphenylchloroarsine (Clark I) and related aromatic arsenicals were used as chemical warfare agents in World Wars I and II. After their use was abandoned, the compounds were often buried, where they were degraded to methylphenylarsinic acid (MPAA), dimethylphenylarsine oxide (DMPAO) and methyldiphenylarsine oxide (MDPAO), perhaps by microbial activity (3, 14).

Thus, a need exists for methods for detecting the presence of organic arsenic.

SUMMARY

In one aspect of the disclosure, there is provided a method of detecting organic arsenic in a sample comprising contacting the sample with a cell comprising (1) a AfArsR protein and (2) a arsR gene and arsO-gfp gene, wherein in the presence of the organic arsenic the cell fluoresces.

In some embodiments of the method, the fluorescence is proportional to the amount of organic arsenic in the sample.

In some embodiments of the method, the sample has a concentration of organic arsenic, as methylarsenite of $10^{-6}$ M to $10^{-5}$ M or as phenylarsenite or trivalent roxarsone of $10^{-8}$ M to $10^{-6}$ M.

In some embodiments of the method, the organic arsenic comprises phenylarsenite, trivalent roxarsone, methylarsenite, or combinations thereof.

In some embodiments of the method, the arsR gene, arsO promoter, or both are from *A. ferrooxidans*.

In some embodiments of the method, the cell comprises the *E. coli* strain AW3110.

In some embodiments, the method further comprises contacting the cell with arabinose.

In some embodiments of the method, the arabinose concentration is 0.05% to 0.5%. In some embodiments, the arabinose concentration is about 0.5% and the method detects methylarsenite at a concentration of 2 to 8 μM. In some embodiments, the arabinose concentration is about 0.05% and the method detects phenylarsenite or trivalent roxarsone at a concentration of 0.1 to 0.5 μM.

In some embodiments of the method, the AfArsR protein lacks Cys102 residue.

In some embodiments of the method, the cell does not fluoresce in the presence of inorganic trivalent arsenic.

In another aspect of the disclosure, there is provided a method of detecting organic arsenic in a sample comprising (1) contacting the sample with a prokaryotic cell comprising a first polynucleotide comprising a coding region for ArsR operably linked to a repressible or an inducible promoter and a second polynucleotide comprising a coding region for a reporter operably linked to an arsenical resistance operon (ars) promoter and (2) detecting expression of the reporter gene.

In some embodiments of the method, the expression of the reporter gene is proportional to the amount of organic arsenic in the sample.

In some embodiments of the method, the sample has a concentration of organic arsenic, as-methylarsenite, of $10^{-6}$ M to $10^{-5}$ M or as phenylarsenite or trivalent roxarsone of $10^{-8}$ M to $10^{-6}$ M.

In some embodiments of the method, the organic arsenic comprises phenylarsenite, trivalent roxarsone, methylarsenite, or combinations thereof.

In some embodiments of the method, the repressible promoter is an ara promoter.

In some embodiments of the method, the polynucleotide comprising a coding region for ArsR is derived from *Acidithiobacillus ferrooxidans*.

In some embodiments of the method, the *A. ferrooxidans* ArsR comprises a mutation in the codon for amino acid 102. In some embodiments, the mutation results in a substitution or deletion. In some embodiments, the substitution results in a serine residue a amino acid 102.

In some embodiments of the method, the ars promoter is an *A. ferrooxidans* arsO promoter.

In some embodiments of the method, the reporter gene is a gfp gene.

In some embodiments of the method, detecting expression of the reporter gene comprises detecting fluorescence.

In some embodiments of the method, the prokaryotic host cell is an *E. coli* strain. In some embodiments, the *E. coli* strain is an arsenic-hypersensitive *E. coli* strain. In some embodiments, the arsenic-hypersensitive *E. coli* strain is AW3110(ars:cam).

In some embodiments, the method further comprises contacting the cell with arabinose. In some embodiments, the arabinose concentration is 0.05% to 0.5%. In some embodiments, the arabinose concentration is about 0.5% and the method detects methylarsenite at a concentration of 2 to 8 µM. In some embodiments, the arabinose concentration is about 0.05% and the method detects phenylarsenite or trivalent roxarsone at a concentration of 0.1 to 0.5 µM.

In some embodiments of the method, the first polynucleotide and the second polynucleotide are the same.

In yet another aspect of the disclosure, there is provided a prokaryotic host cell comprising (a) a first polynucleotide comprising a coding region for ArsR operably linked to a repressible or an inducible promoter and (b) a second polynucleotide comprising a coding region for a reporter operably linked to an arsenical resistance operon (ars) promoter.

In some embodiments, the repressible promoter is an ara promoter.

In some embodiments, the polynucleotide comprising a coding region for ArsR is derived from *Acidithiobacillus ferrooxidans*. In some embodiments, the *A. ferrooxidans* ArsR comprises a mutation in the codon for amino acid 102.

In some embodiments, the mutation is a substitution or deletion. In some embodiments, the substitution results in a serine substitution at amino acid 102.

In some embodiments, the ars promoter is an *A. ferrooxidans* arsO promoter.

In some embodiments, the reporter gene is a gfp gene.

In some embodiments, the prokaryotic host cell is an *E. coli* strain. In some embodiments, the *E. coli* strain is an arsenic-hypersensitive *E. coli* strain. In some embodiments, the arsenic-hypersensitive *E. coli* strain is AW3110(ars:cam).

In some embodiments, the first polynucleotide and the second polynucleotide are the same.

Other features and advantages of the present disclosure will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description. The entire document is intended to be related as a unified disclosure, and it should be understood that all combinations of features described herein are contemplated, even if the combination of features are not found together in the same sentence, or paragraph, or section of this document. In addition to the foregoing, the invention includes, as an additional aspect, all embodiments of the invention narrower in scope in any way than the variations specifically mentioned above. For example, if aspects of the invention are described as "comprising" a feature, embodiments also are contemplated "consisting of" or "consisting essentially of" the feature.

BRIEF DESCRIPTION OF THE FIGURES

FIG. 11 shows that AfArsR dissociation from the DNA was induced by addition of the indicated concentrations of arsenicals: (●), MAs(III); (▼), As(III); ( ), MAs(V); (▲), PAO; (■), Rox(III). As controls, the effect of each arsenical on the anisotropy of the fluorescently labeled DNA was measured in the absence of AfArsR: (O), MAs(III); ( ), As(III); ( ), MAs(V); (Δ), PAO; (□), Rox(III).

FIG. 13: Comparison of the response of the bacterial biosensor to inorganic and organic arsenicals. A) To amplify the signal, the minimum concentration of arabinose required to repress gfp expression was determined. Cells were grown as described below with the indicated concentrations of arabinose in the absence of arsenical inducer. B) Cells were grown in LB medium in the absence of arabinose or with 0.05% arabinose and the indicated concentrations of arsenicals. The concentration of inducers was adjusted to prevent toxicity, and the fluorescence intensities were measured by spectrofluorometry. C) Cells were grown in LB medium with 0.2% arabinose and the indicated concentrations of inducers: (O), MAs(III); (V), As(III); (Δ), PAO; ( . . . ), Rox(III).

FIG. 16A: Response of the bacterial biosensor responded to phenylarsonic acid (PAO). Expression of the gfp reporter gene was assayed as described below. Cells were grown in LB medium without or with 0.05% arabinose in the present of arsenicals for 14 hr, centrifuged and visualized with a hand-held lamp under visible (up) or UV (down) light. (B)

FIG. 16B: Response of the bacterial biosensor or biosensor co-cultured with *Burkholderia* responded to organic arsenicals. Expression of the gfp reporter gene was assayed as described below. Biosensor or co-cultured with *Burkholderia* were grown in M9 medium without or with 0.05% arabinose in the present of organic arsenicals for 14 hr, centrifuged and visualized with a hand-held lamp under visible (up) or UV (down) light.

DETAILED DESCRIPTION

Figure 1:
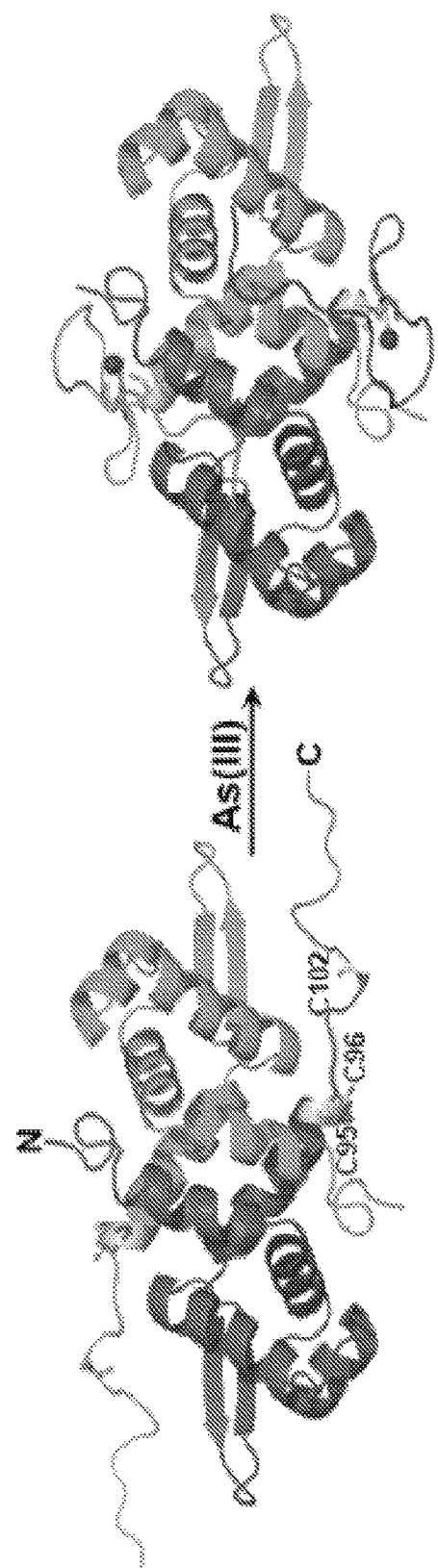
FIG. 1 shows a structural model of the AfArsR repressor. Homology models of the AfArsR homodimer was constructed using the crystal structure of the homologue CadC (33) as template (16). The two monomers are shaded. The cysteines are shown in sticks. The As(III)s are shown in spheres. AfArsR binds an arsenic atom at each end of the two α5 helices to the thiolates of Cys95, Cys96 and Cys102.

Provided herein is biosensor that detects trivalent organoarsenics and discriminates between organic and inorganic arsenic. Current detection methods for total organic arsenicals in biological samples involve oxidative digestion of the organic matrix into inorganic arsenic, which is quantified by analytical laboratory techniques such as inductively coupled mass spectroscopy (ICP-MS). These laboratory-based spectroscopic methods are costly and require skillful operators. Commercial chemical field test kits are used in countries such as Bangladesh and India with varying degrees of success (19). The principle of these kits is the formation of volatile arsine gas ($AsH_3$) to separate arsenic from the aqueous matrix and subsequent colorimetric detection on a paper strip (12). However, these test kits have low precision, poor reproducibility, high rates of false positives and negatives, and accuracy is limited to concentrations between the EPA maximum containment level and World Health Organization (WHO) maximum allowable concentration for arsenic in drinking water of 10 ppb (0.13 pM) up to 100 ppb (1.33 pM) (9).

Whole-cell bacterial biosensors have been proposed as an alternative, rapid, cost-effective and high-throughput method to measure arsenic in aquatic samples (22). Bacterial biosensors rely on the ability of cells to produce a detectable signal that can serve as a reporter of a particular environmental condition. Most reported arsenic biosensors utilize the As(III)-responsive transcriptional repressor ArsR first described from our laboratory (24, 31) to control expression of reporter genes. ArsR binds to the ars operator/promoter, preventing transcription of the ars genes for arsenic detoxification. When bacterial cells are exposed to environmental until As(III) or Sb(III), ArsR binds the trivalent metalloid, which produces a conformational change that results in dissociation of the repressor from the DNA, and, in turn results in expression of the genes driven by the ars promoter. ArsR has previously been used for construction of bacterial biosensors for detection of inorganic arsenic using luxAB (20) and electrochemistry (25). In addition, a ArsR homologue CadC, a Cd(II)/Pb(II)/Zn(II)-responsive transcriptional repressor, has been used for construction of a biosensor that uses gfp (encoding the *Aequorea victoria* gene for green fluorescent protein) to sense heavy metals (26, 29).

However, currently available whole-cell bacterial biosensors detect only trivalent inorganic arsenic. No sensor of organic derivatives of arsenic has been described, and the objective of this study was construction of a biosensor with the capability first, of sensing organic arsenicals, and second, exhibiting selectivity between the inorganic and organic species. It has been shown that PAO induces expression of the ars operon of *E. coli* (32) by binding to the ArsR repressor (27), suggesting that ArsR may be suitable for construction of an organoarsenical biosensor.

Provided herein is a two-plasmid biosensor that utilizes the AfarsR gene encoding the As(III)-responsive repressor from *Acidithiobacillus ferrooxidans* (16) to control gfp expression. Purified AfArsR has previously been shown to bind to the ars operator/promoter. When As(III) binds to Cys95, Cys96 and Cys102 of AfArsR, a conformational change is produced in the C-terminal dimerization domain helix (FIG. 1). The change in repressor conformation results in its dissociation from the arsO operator/promoter and hence gene expression. This sensor can discriminate between the aromatic arsenical PAO, MAs(III) and inorganic As(III). The results from both in vitro DNA binding assays and in vivo gfp expression assays show that this sensor responds to trivalent arsenicals in the order PAO>>MAs(III)>As(III). By titrating intracellular levels of AfArsR, the biosensor becomes nearly completely selective for either the aromatic arsenical PAO or methylarsenite, with little response to inorganic arsenic, providing the first bacterial biosensor that is selective for organic derivatives of arsenic. This biosensor may prove useful in detecting the products of biotransformation of arsenical herbicides and animal growth promoters and their mobility in agricultural settings.

Pentavalent organic arsenicals are used as herbicides (MAs(V)) and in animal feed as antimicrobial agents such as 3-Nitro® (or 4-hydroxy-3-nitrobenzenearsonic acid or Roxarsone). Both pentavalent arsenicals are more stable to atmospheric oxidation than trivalent arsenicals, which is why they can be successfully applied in agriculture and animal husbandry. Intracellularly As(V) is reduced to the more toxic As(III) (15), and we hypothesize that the pentavalent organic species are taken into cells, where they are transformed to trivalent species that are the active herbicides or antimicrobials. Analogously, the pentavalent antileishmanial prodrug pentostam, which contains the metalloid Sb(V), is biotransformed in the parasite by to Sb(III), the active form of the drug (37). Additionally, biotransformation is essential for degradation of these herbicides and antimicrobials (28, 36), where trivalent species can be breakdown products. The trivalent aromatic arsenical Clark I was used as a chemical warfare agent, and it is also broken down in soil, probably as the result of microbial action (3, 14). Extrapolating from the ability of the bacterial biosensor to sense phenylarsenite, the disclosed biosensors are therefore capable of sensing the breakdown products of the related organoarsenicals Roxarsone and Clarke I. Monitoring the prevalence of these environmentally pervasive organoarsenicals requires methods for detection of organic arsenic species in the field.

Currently available methods for field testing rely on either chemical or biological techniques and determine only inorganic arsenic or total arsenic if the samples are first digested to inorganic arsenic. Chemical test kits have low precision, reproducibility and accuracy at arsenic concentrations between 10 pg/L and 100 pg/L (9). They also have some limitations with interfering elements. Bacterial biosensors have been proposed as an alternative, rapid, high-throughput and cost-effective method to measure inorganic As(III) in potable water.

Most of these arsenic biosensors utilize the As(III)-responsive transcriptional repressor ArsR first described from our laboratory (24, 31) to control expression of reporter genes. They are selective for arsenic over every other element but antimony. Currently cell based biosensors have not been shown to sense methylarsenicals either generated biologically or applied as herbicides or the aromatic arsenicals that are used as feed supplements or chemical warfare agents.

Figure 2:
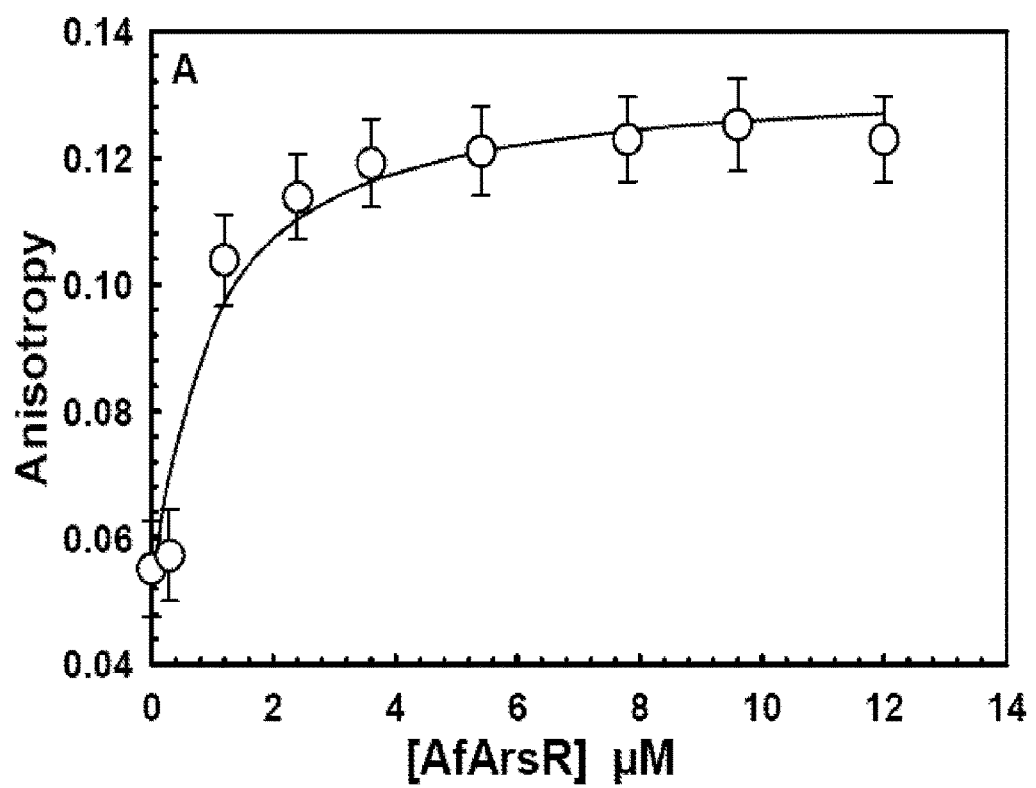
FIG. 2 shows the effect of arsenicals on AfArsR binding to DNA. DNA binding assays were performed as described below. A) Fluorescently labeled double stranded DNA was titrated with the indicated concentrations of AfArsR (O). B and C) AfArsR dissociation from the DNA was induced by addition of the indicated concentrations of arsenicals: (●), MAs(III); (○), As(IIII); (□), MAs(V). As controls, the effect of each arsenical on the anisotropy of the fluorescently labeled DNA was measured in the absence of AfArsR: (▼), MAs(III), (Δ), As(III); (■), MAs(V).
Figure 8:
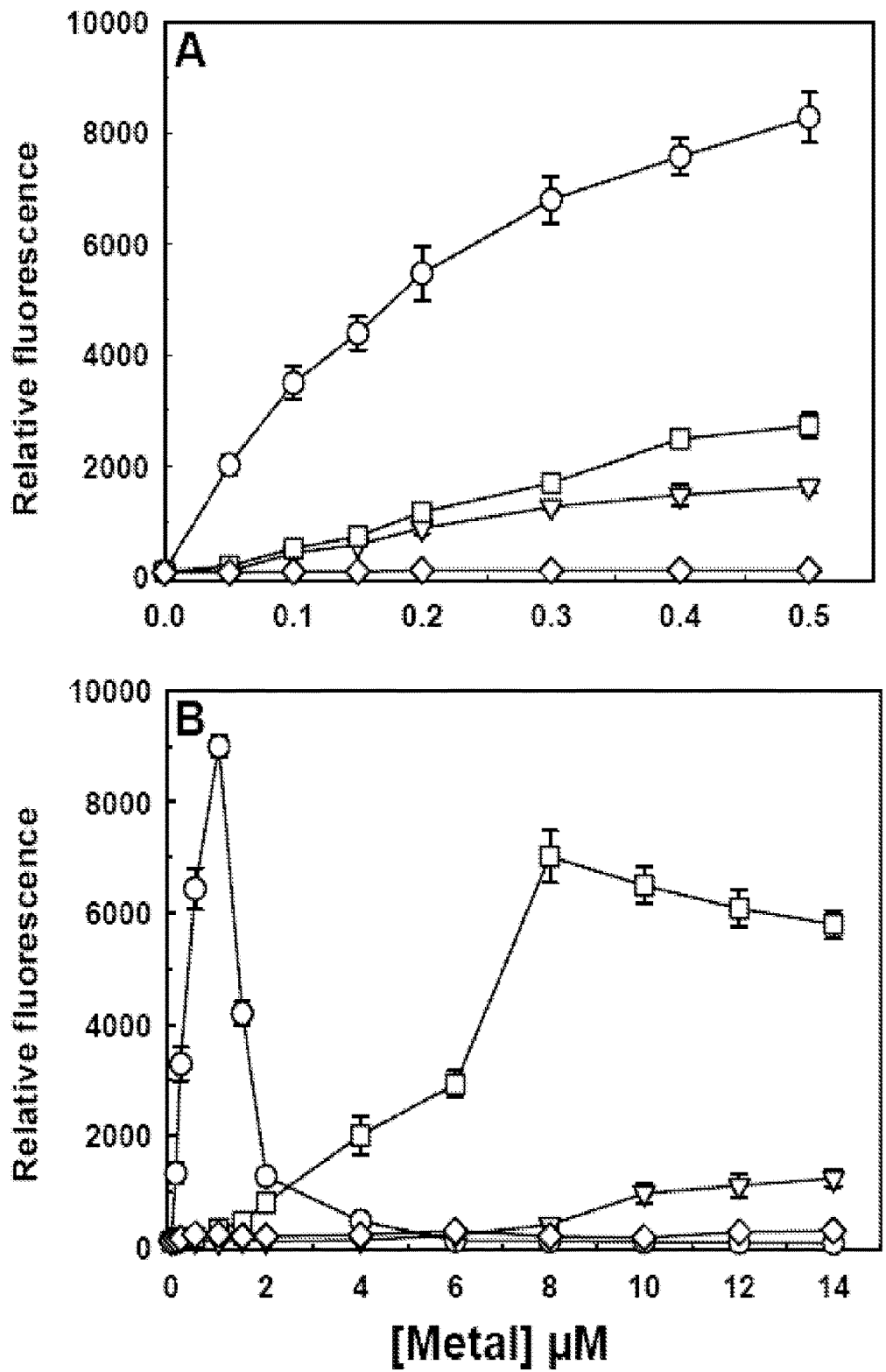
FIG. 8 shows tuning the bacterial biosensor for either higher sensitivity or greater selectivity. A) At low arabinose concentration (0.05%), the biosensor was highly selective for PAO. B) At high arabinose concentration (0.5%), the sensor was highly selective for MAs(III) over As(III). (O), PAO; (□), MAs(III); (∇), MAs(IIII), (◇), MAs(V).

To construct a cell-based biosensor that was both more sensitive to arsenic than currently available sensors but could also be highly selective for organic arsenic species, we focused on an ArsR orthologue, AfArsR from *A. ferrooxidans* (16). AfArsR lacks the As(III) binding site of the *E. coli* ArsR, which is composed of Cys32, Cys34 and Cys37 in the DNA binding site (27). *E. coli* ArsR is induced by PAO (32), which suggested that ArsR might be useful as an organoarsenical biosensor. However, only Cys32 and Cys37 are required; there is no effect of substitution of Cys37 on binding of As(III), so the *E. coli* ArsR might not be able to distinguish between As(III) and PAO or MAs(III). In contrast, AfArsR has three cysteine residues, Cys95, Cys96 and Cys102, located in the C-terminal dimerization domain of the repressor (FIG. 1). Cys95 and Cys96 are required for As(III) regulation, but Cys102 appears to have a role in modulating affinity. Cys95 and Cys96 are in an a helix that is predicted to unwind before it can bind arsenic, and it is this conformation change that is proposed to be responsible for induction. This suggested that arsenicals such as MAs(III) that have only two coordinations available for binding to ArsR might bind to Cys95 and Cys96 with higher affinity than As(III). In support of this idea, in vitro purified AfArsR bound MAs(IH) with 4-fold higher affinity than inorganic As(III) (FIG. 2B). The in vivo bacterial biosensor was very sensitive, exhibiting a linear response to inorganic As(III) concentrations around the WHO and EPA limits of 10 ppb (FIG. 8A).

More importantly, the biosensor provides an analog response to organic arsenicals. The response is modulated by adjusting the concentration of arabinose, which regulates AfarsR and, in turn, gfp expression. The biosensor can be made specific for either MAs(III), which is a degradation product of the herbicide MAs(V), or for trivalent PAO, which is related to aromatic arsenical chemical warfare agent Clark I and growth enhancers such as Roxarsone, both of which are broken down environmentally. Roxarsone is degraded to inorganic arsenic (28), and we predict that intermediates in its breakdown will be trivalent phenylarsenicals related to PAO that the biosensor can detect. Thus, construction of a bacterial biosensor for organic arsenicals demonstrates that it should be possible to design field test kits for organic arsenicals. In addition, we have genetically modified AfArsR to change Cys102 to another residue. The mutant AfArsR no longer recognizes inorganic As(III) but still senses MAs(III) and PAO. This mutant can be the basis for a biosensor with high specificity for organoarsenicals.

The detection of organoarsenicals can be performed in the presence of AfArsR, or a mutant AfArsR, and arabinose. In some cases, the arabinose is present at up to 0.02%, up to 0.05%, up to 0.1%, or up to 0.5%.

Pentavalent organic arsenicals are used as herbicides (MAs(V)) and in animal feed as antimicrobial agents (e.g., Roxarsone). Both pentavalent arsenicals are more stable to atmospheric oxidation than trivalent arsenicals, which is why they can be successfully applied in agriculture and animal husbandry. Intracellularly of cells As(V) is reduced to the more toxic As(III), and it is hypothesized that the pentavalent organic species are taken into cells, where they are transformed to trivalent species that are the active herbicides or antimicrobials. Analogously, the pentavalent antileishmanial prodrug pentostam, which contains the metalloid Sb(V), is biotransformed in the parasite by to Sb(III), the active form of the drug. Additionally, biotransformation is key for degradation of these herbicides and antimicrobials, where trivalent species can be breakdown products. Monitoring the prevalence of these environmentally pervasive arsenicals requires methods for detection of organic arsenic species in the field.

Currently available methods for field testing rely on either chemical or biological techniques and determine only inorganic arsenic or total arsenic if the samples are first digested to inorganic arsenic. Chemical test kits have low precision, reproducibility and accuracy at arsenic concentrations between 10 µg/lL and 100 µg/L. They also have some limitations with interfering elements. Bacterial biosensors have been proposed as an alternative, rapid, high-throughput and cost-effective method to measure inorganic As(III) in potable water. Most of these arsenic biosensors utilize the As(III)-responsive transcriptional repressor ArsR to control expression of reporter genes. They are selective for arsenic over every other element but antimony. Currently most of cell based biosensors have not been shown to sense methylarsenicals either generated biologically or applied as herbicides or the phenylarsenicals that are used as feed supplements.

Figure 14:
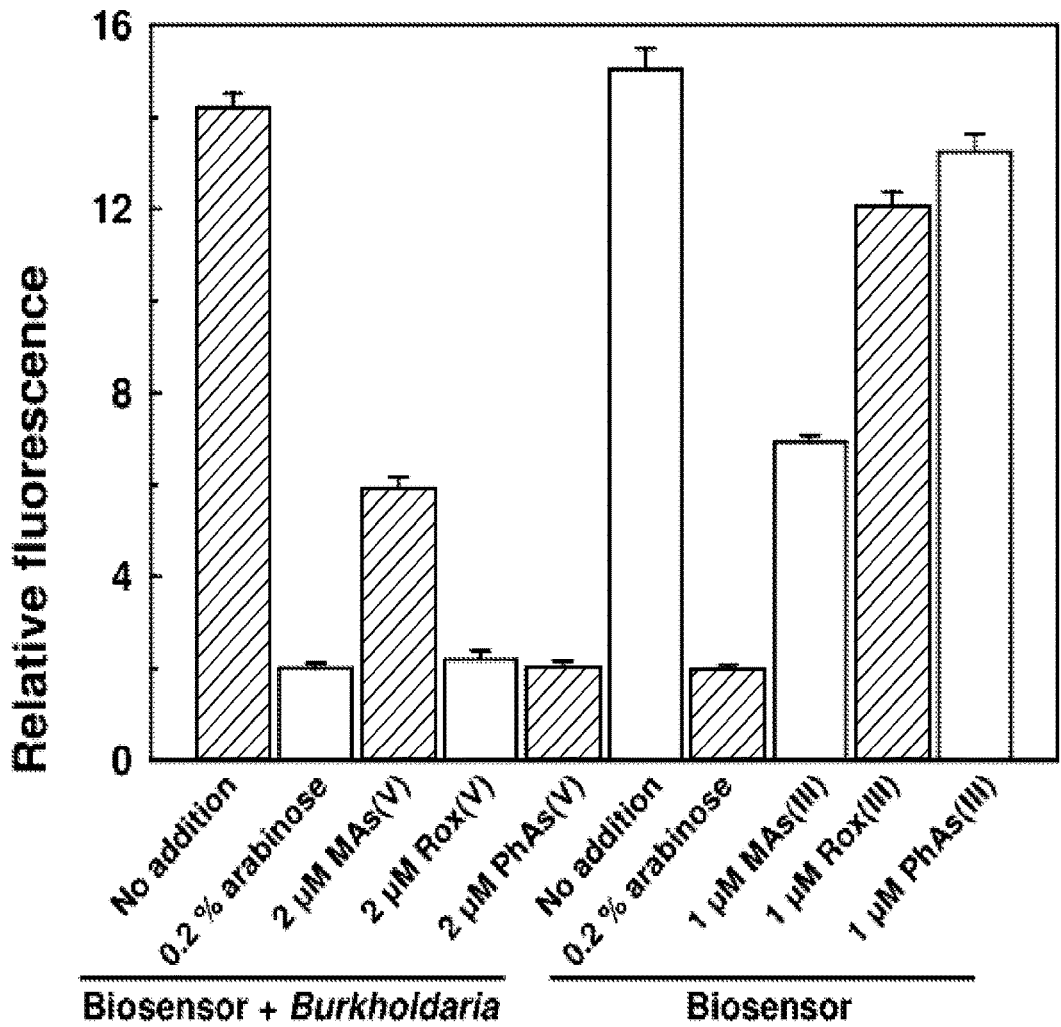
FIG. 14: Biosensor respond to MAs(V) by co-cultured with *Burkholderia* sp.MR1. To amplify the signal, 0.05% arabinose was used to induce AfArsR C102S mutant expression. Biosensor and *Burkholderia* were grown in M9 medium supplemented with 0.5% glycerol as carbon source, and incubated with the indicated concentrations of inorganic arsenic overnight, following which the fluorescence intensity was quantified by spectrofluorometry.

Provided herein is a cell-based biosensor that is both more sensitive to arsenic than currently available sensors but could also be highly selective for organic arsenic species, using an ArsR ortholog, AfArsR from *A. ferrooxidans*. AfArsR lacks the As(III) binding site of the *E. coli* ArsR, which is composed of Cys32, Cys34 and Cys37 in the DNA binding site. The *E. coli* ArsR is induced by PAO, which suggests that ArsR can be useful as an organoarsenical biosensor. However, only Cys32 and Cys37 are required; there is no effect of substitution of Cys37 on binding of As(III), so the *E. coli* ArsR might not be able to distinguish between As(III) and PAO or MAs(III). In contrast, AfArsR has three cysteine residues, Cys95, Cys96 and Cys102, located in the C-terminal dimerization domain of the repressor (FIG. 1). Cys95 and Cys96 are required for As(III) regulation, but Cys102 appears to have a role in modulating affinity. Cys95 and Cys96 are in an α helix that must unwind to be able to bind arsenic, and it is this conformation change that is proposed to be responsible for induction. This suggested that arsenicals such as MAs(III) that have only two coordination sites available for binding to ArsR might bind to Cys95 and Cys96 with higher affinity than As(III). In support of this idea, in vitro purified AfArsR bound MAs(III) with 4-fold higher affinity than inorganic As(III) (FIGS. 11A and B). In vitro purified AfArsR C102S mutant lost its binding ability for As(III), but it showed the same binding affinity for phenoarsenical and methylarsenite, as well as wild type AfArsR (FIGS. 11C and 11D). The in vivo bacterial biosensor with wild type AfArsR was very sensitive, exhibiting a linear response to inorganic As(III) concentrations around the WHO and EPA limits of 10 ppb and the response is modulated by adjusting the concentration of arabinose, which regulates AfarsR and, in turn, gfp expression. But the biosensor with C102S mutant can be made directly specific for either MAs(III), which is a degradation product of the herbicide MAs(V), or for trivalent PAO and Rox(III), which is related to phenylarsenical growth enhancers such as roxarsone. Roxarsone is degraded to inorganic arsenic, and it is predicted that intermediates in its breakdown will be trivalent phenylarsenicals related to PAO that the biosensor can detect (FIGS. 14 and 16A). Compared to the biosensor with wild type AfArsR, there is no need to increase the expression of AfArsR to turning the selectivity, which will decrease the sensitivity. So this biosensor with C102S mutant will show more accurate results due to lower expression AfArsR. Thus, construction of a bacterial biosensor for organic arsenicals demonstrates that it should be possible to design field test kits for organic arsenicals.

The microbial soil community in the contaminated regions plays a significant role in the arsenic biogeocycle, yet little is known about mechanisms of biotransformation. Methylarsonic acid (MAs(V)), can be converted to more toxic MAs(III), which could be reduced by *Burkholderia* and other organisms. When co-cultured the biosensor and *Burkholderia* with MAs(V), it conferred the cell mixtures with fluorescence, but it didn't when added with Rox(V) and PAA, It demonstrated that *Burkholderia* couldn't reduced Rox(V) and PAA. Although MAs(V) can be reduced by *Burkholderia* sp.MR1 or *Pseudomonas putida* KT2440, the mechanism of the reduction process is still unknown. It is convenient to use this biosensor to screen the functional gene, which catalyzes the process from its cDNA library.

Figure 16C:
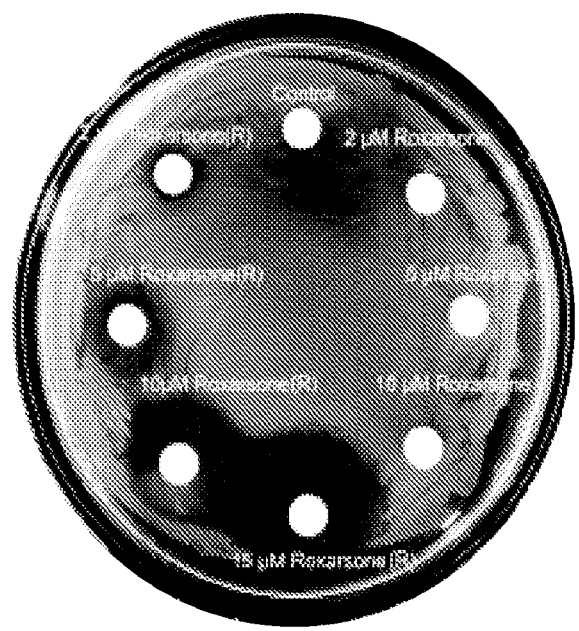
FIG. 16C: The toxicity of Rox(III) was checked by disk test. 100 μL biosensor was sprayed evenly on the LB plate After 30 min, Rox(V) and Rox(III) with different concentrations were added to the disks, then incubated overnight.

Rox(III) and PAO are toxic products (FIG. 16C). It is also promising to use this biosensor for screening the microorganisms which play an important role in the process of Rox(V) and PAA biotransformation.

Strain, plasmids, medium, and reagents. *E. coli* cells were grown aerobically in Luria-Bertani (LB) medium (23) at 37 C supplemented with 100 pa/ml amp cillin, 12.5 pg/ml tetracycline, or 34 pg/ml chloramphenicol, as required. *E. coli* strains DH5a (Promega, Madison, Wis.) was used for plasmid construction and replication. *E. coli* strain Top10 (Invitrogen, Grand Island, N.Y.) was used for protein expression. Plasmids pGREEN (John Innes Centre, Norwich, UK), pBAD (Invitrogen, Grand Island, N.Y.), pACYC184 (6), and *E. coli* strain AW3110(DE3) (AarsRBC) (5) were used to construct the biosensor. The biosensor strain had two plasmids, pACYC184-parsO-gfp and pBADarsR (either wild type or C102S AfarsR genes). Bacterial growth was monitored by measuring the $A_{600}$ nm. All reagents were obtained from commercial sources.

AfArsR purification. Cells of *E. coli* strain Top 10 bearing pBADarsR plasmids were grown at 37° C. in LB medium to an $A_{600}$ nm of 0.5, at which point 0.2% arabinose was added as inducer. The cells were grown for another 4 h and harvested by centrifugation at 4° C., washed once with buffer A (50 mM MOPS-KOH, pH 7.5, containing 20% (w/v) glycerol, 0.5 M NaCl. 20 mM imidazole, and 10 mM 2-mercaptoethanol), and suspended in 5 mL of buffer A/g of wet cells. The cells were lysed by a single pass through a French Press cell at 20,000 p.s.i. and 2.5 Wig of wet cell of di-isopropyl fluorophosphate was added immediately. Membranes and unbroken cells were removed by centrifugation at 150,000×g for 1 h, and the supernatant solution was loaded at a flow rate of 0.5 ml/min onto a Ni(II)-nitrilotriacetic acid column pre-equilibrated with buffer A. The column was then washed with 150 ml of buffer followed by elution with 60 mL of buffer A with the concentration of imidazole increased to 0.2 M. The eluted protein was concentrated with a 10-kDa cut-off Arnicon Uftracentrifugal filter (Millipore Corp., Billerica, Mass.). The concentrated protein was further purified by gel filtration using Superdex 75 (Amersham Biosciences) in a 45×1.5-cm column with a total bed volume of 80 ml. The protein was eluted with buffer A containing 0.2 mM EDTA at a flow rate of 0.3 ml/min. AfArsR was identified by SDS-PAGE (13). Fractions containing AfArsR were concentrated by ultrafiltration centrifugation. Protein concentrations were estimated using the method of Bradford (4) or from A280 using a calculated extinction coefficient of 4,200 $crn^{-1}$ (10).

Fluorescence anisotropy. DNA binding studies by fluorescence anisotropy were performed using a Photon Technology International spectrofluorometer fitted with polarizers in the L format. Changes in anisotropy were calculated after each addition using the supplied Felix32 software. Complementary 30-mer oligonucleotides, one of which was labeled at the 5'end with fluorescein were synthesized (Integrated DNA Technologies, Inc. Coralville, Iowa) with the following sequences: 6-FAM-5'-ATCCACGAATATTTCTT-GCAGTATTGACAA-3' and 5'-TAGGTGCT-TATAAAGAACGTCATAACTGTT-3' (16). Desalted DNA was annealed at 94° C. for 5 min, cooled to room temperature, and stored in aliquots at −20° C. Anisotropy measurements were performed in a buffer consisting of 10 mM MOPS-NaOH, pH7.5, containing 0.1 M NaCl, 15% glycerol, and 250 nM DNA. AfArsR was titrated with 50 nM fluorescein-labeled arsO DNA and metallated by mixing 1 M equivalent of AfArsR with the indicated concentrations of As(III), MAs(III) or MAs(V) under anaerobic conditions.

Construction of the bacterial biosensor. Plasmid pBA-DarsR (16), in which the AfarsR gene from *A. ferrooxidans* is under control of the arabinose promoter and has the sequence for a C-terminal His tag, was used for AfArsR expression. It is understood that the arabinose promoter is simply a representative example, and any suitable promoter can be used. It is also understood that promoters include operators, which can include repressor and/or inducer binding sites.

Plasmid pACYC184-parsO-gfp, in which the gfp reporter gene was fused to the *A. ferrooxidans* arsO promoter was constructed in two steps. First, the arsO promoter from pACYC184lacZ-arsO (16) was amplified by PCR using forward and reverse primers 5'-GCTCTAGACTTCGCGCT-GCACGGTGA-3' (XbaI site underlined) and 5'-GCG-GATCCGCTTGGAGGAACTCCGGA-3' (BamHI site underlined). Second, the gfp gene was cloned from vector plasmid pGreen (Carolina Biological Supply Company, Burlington, N.C.) using forward and reverse primers 5'-GCG-GATCCATGAGTAAAGGAGAAGAA C TTTT-3' (BamHI site underlined) and 5'-GCGTCGACCGAGCTCGAATTC-TAC-3' (SalI site underlined). The two PCR fragments were gel purified, digested with restriction enzymes corresponding to the underlined sites and ligated in frame into vector plasmid pACYC184 that had been digested with the same restriction enzymes, generating plasmid pACYC184-parsO-gfp. Plasmids pBADarsR and pACYC184-parsO-gfp were transformed simultaneously into *E. coli* strain AW3110, and tranformants were isolated on LB plates with ampicillin and chloramphenicol. Colonies fluorescent under UV light (365 nm) were purified for further analysis.

The transcriptional activity of the biosensor was estimated from the fluorescence of cells grown in LB medium containing the indicated additions using a spectrofluorometer with an excitation wavelength of 470 nm and emission wavelength of 510 nm. Cultures of *E. coli* strain AW3110 bearing plasmids pBADarsR and pACYC184-pars0-gfp were grown in LB medium at 37° C. in a reciprocating shaker with ampicillin and chloramphenicol. Growth in the presence of 0.2% glucose allowed for constitutive expression of gfp. AfArsR was induced by addition of the indicated concentrations of arabinose. Derepression was produced by simultaneous addition of arabinose and arsenicals.

In vitro biosensor assays. Wild type AfArsR and the C120S derivative were purified from cells of *E. coli* strain Top10 (Invitrogen, Grand Island, N.Y.) bearing pBADarsR plasmids. AfArsR binding to DNA and dissociation by inducers was assayed by fluorescence anisotropy using a Photon Technology International spectrofluorometer fitted with polarizers in the L format. Changes in anisotropy were calculated after each addition using the supplied Felix32 software. Complementary 30-mer oligonucleotides, one of which was labeled at the 5'end with fluorescein, were synthesized (Integrated DNA Technologies, Inc., Coralville, Iowa) with the following sequences: 6-FAM-5'-ATCCAC-GAATATTTCTTGCAGTATTGACAA-3' and 5-TAGGT-GCTTATAAAGAACGTCATAACTGTT-3'. Desalted DNA was annealed at 94° C. for 5 min, cooled to room temperature, and stored in aliquots at −20° C. Anisotropy measurements were performed in a buffer consisting of 10 mM MOPS-NaOH, pH7.5, containing 0.1 M NaCl, 15% glycerol, and 250 nM DNA. AfArsR was titrated with 50 nM fluorescein-labeled arsO DNA and metallated by mixing 1 molar equivalent of AfArsR with the indicated concentrations of As(III), MAs(III), MAs(V), PhAs(III) or Rox(III) under anaerobic conditions.

In vivo biosensor assays. Transcriptional activity of the biosensor was estimated from arsenical-responsive expression of gfp. Cultures of the biosensor (*E. coli* strain AW3110 bearing plasmids pBADarsR and pACYC184-parsO-gfp) were grown in LB medium at 37° C. with 100 μg/ml ampicillin and 34 μg/ml chloramphenicol with shaking. 0.2% glucose was added for constitutive expression of gfp. Wild type or C102S AfArsR was induced by addition of the indicated concentrations of arabinose. Derepression was produced by simultaneous addition of arabinose and arsenicals. Expression of gfp was assayed from the fluorescence of cells using a spectrofluorometer with an excitation wavelength of 470 nm and emission wavelength of 510 nm.

For in situ methylation of As(III), the biosensor strain was co-cultured with *E. coli* AW3110(DE3) pET28CrarsM, which expressed the *Chlamydomonas reinhardtii* As(III)-S-adenosylmethionine methyltransferase arsM gene encoding the CrArsM As(III) S-adenosylmethionine (SAM) methyltransferase. For in situ reduction of MAs(V), the biosensor strain was co-cultured with *Burkholderia* sp. MR1 in M9 medium at 23° C. with shaking.

Results

AfArsR responds in vitro to MAs(III) and As(III). ArsR binding to DNA and dissociation upon binding of arsenicals was examined by a fluorescence anisotropy assay (16). In this assay, when AfArsR binds to the DNA molecule, the rotation of the larger protein-DNA complex is slower than the rotation of free DNA, producing an increase in anisotropy. The anisotropy of the fluorescein-labeled ars operator/promoter DNA increased as a function of the concentration of AfArsR, with a $K_d$ values of 0.87 pM (FIG. 2A). The effects of addition of MAs(V), MAs(III) and As(III) were compared (FIGS. 2B and C). There was no effect of MAs(V) (or As(V); data not shown) on anisotropy of the AfArsR-DNA complex (FIG. 2B). MAs(III) decreased anisotropy with a half-maximal concentration of approximately 2.5 pM (FIG. 1B), while approximately 10 11M As(III) was required, a four-fold difference in trivalent metalloid binding affinity (FIG. 2C). These results demonstrate that the MAs (III) binds to AfArsR and dissociates it from DNA more effectively than does As(Ill) binding.

Figure 3:
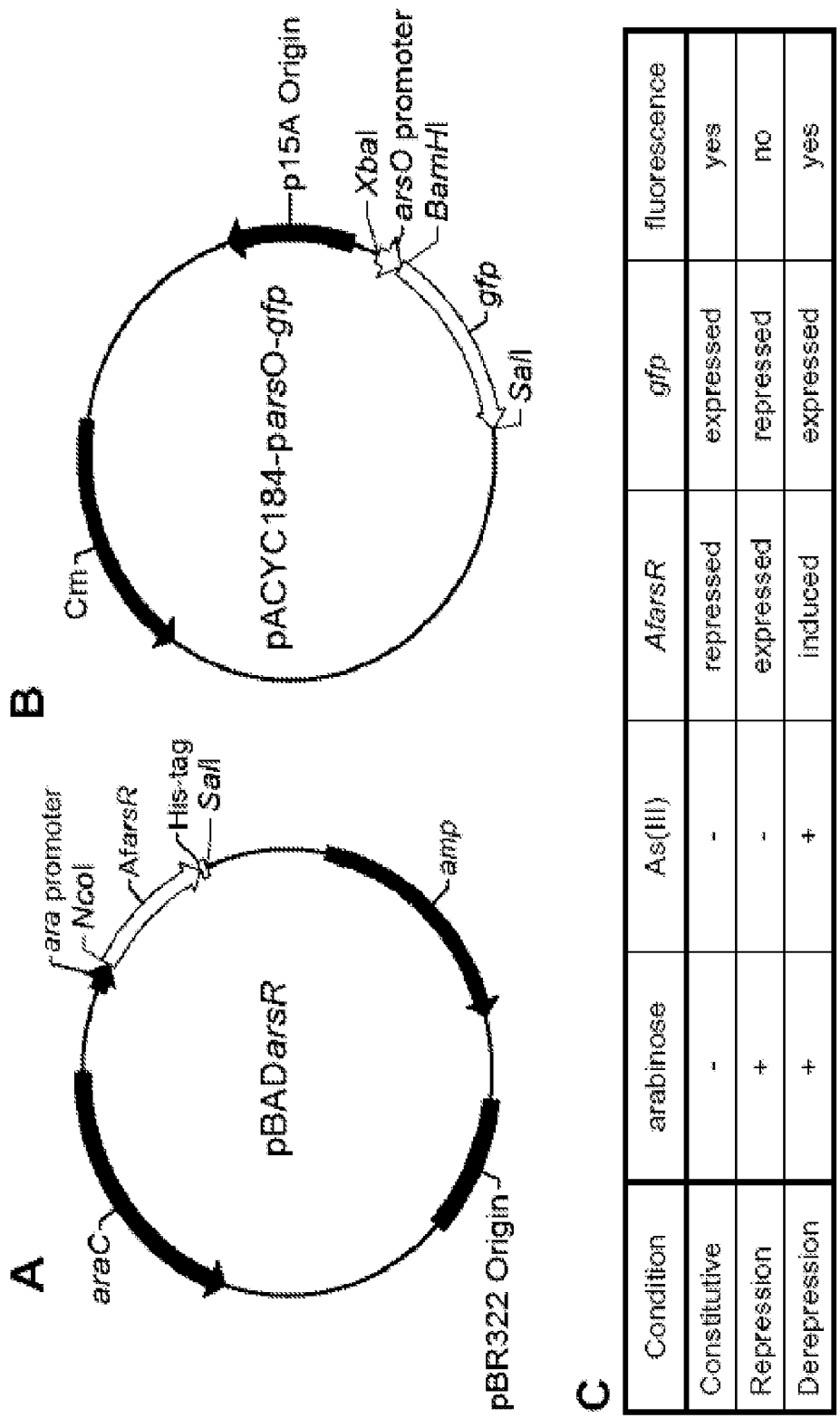
FIG. 3 shows the two plasmids of the biosensor. A) In pBADarsR, AfarsR is under control of the arabinose (ara) promoter. B) In pACYC184-parsO-gfp, the gfp reporter gene is under control of the arsenical resistance operon (ars) promoter, C) Conditions for constitutive, repressed and derepressed gfp expression. In cells of *E. coli* AW3110 with both plasmids, AfarsR is not expressed in the absence of arabinose, and gfp expression is constitutive, with cellular fluorescence. In the presence of arabinose, AfarsR is expressed, and gfp is repressed, so the cells are not fluorescent. In the presence of both arabinose and arsenical inducer, gfp expression is derepressed, and the cells are fluorescent.
Figure 4:
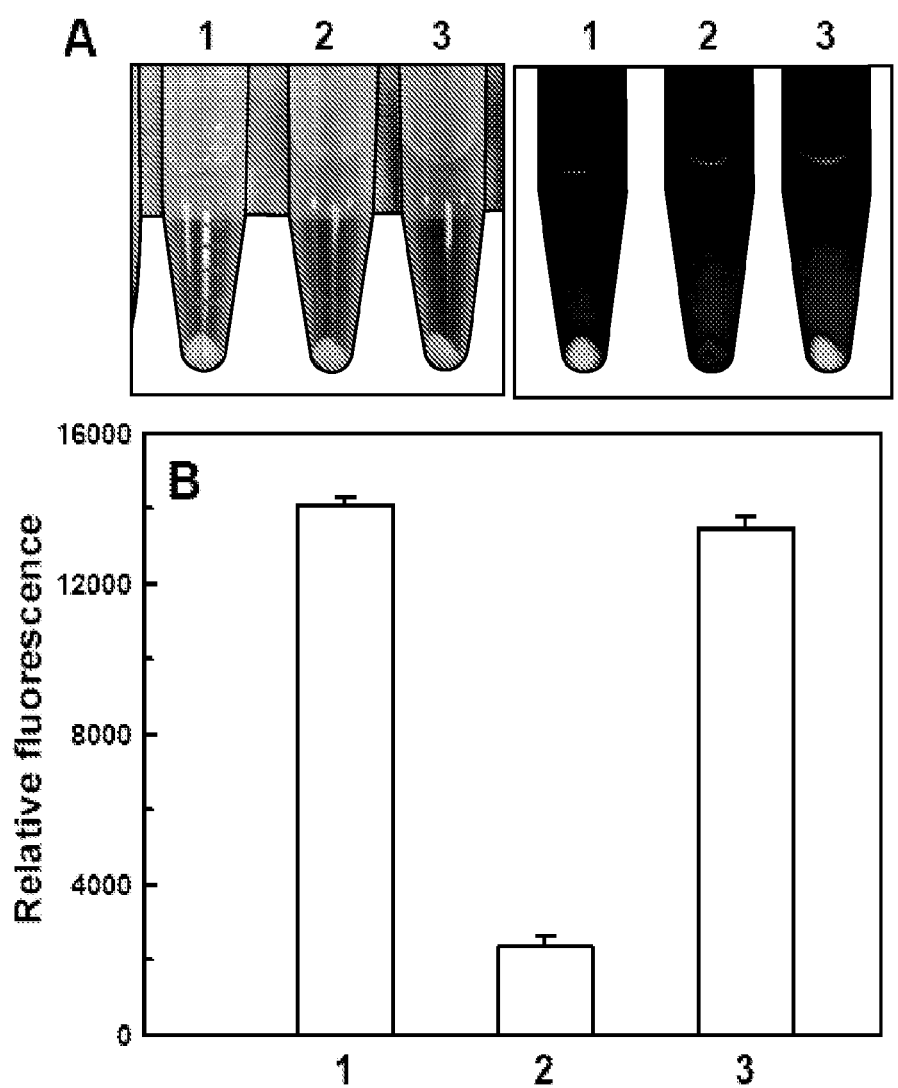
FIG. 4 shows the response of the bacterial biosensor to As(III). Expression of the gfp reporter gene was assayed as described below. A) Effect of arabinose and As(III) on fluorescence of the biosensor cells under white light and UV light. Cells were grown in LB medium for 14 hr, centrifuged and visualized with a hand-held lamp under visible (left) or UV (right) light. 1) No arabinose: 2) 0.2% arabinose; 3) 0.2% arabinose+20 µM inorganic As(III). B. Fluorescence intensities were quantified by spectrofluorometry.
Figure 5:
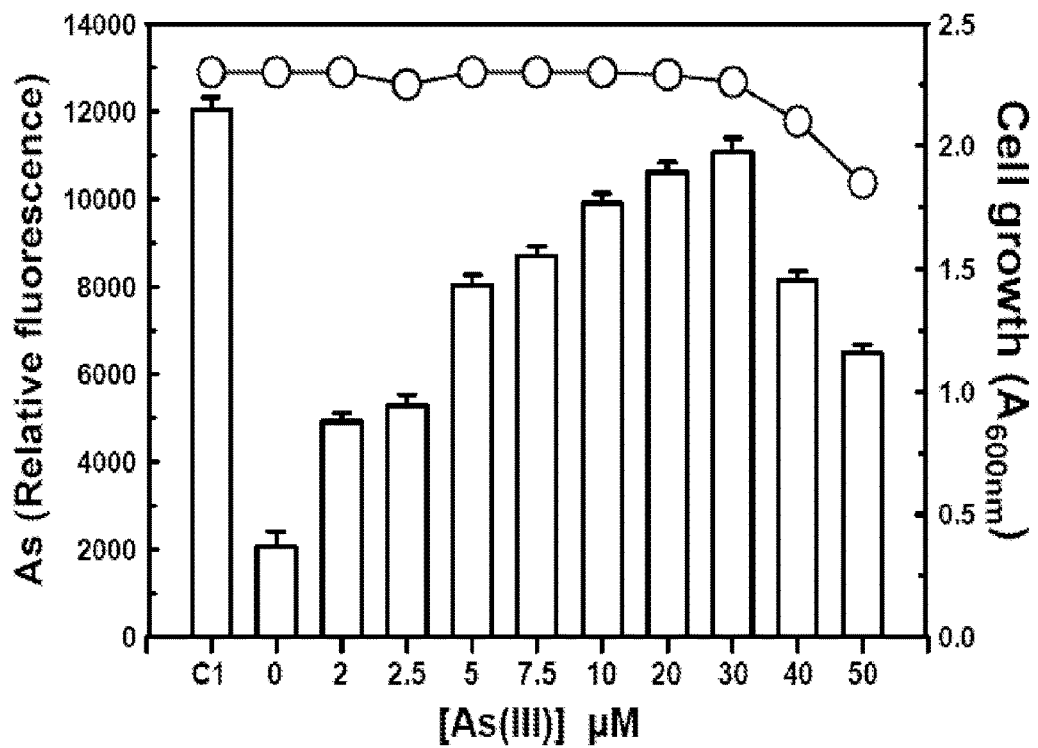
FIG. 5 shows titration of the biosensor response with As(III). Cells were grown in LB medium in the absence of arabinose (C1) or with 0.2% arabinose and the indicated concentrations of inorganic arsenic. Cell growth (O) was monitored after 14 h incubation, and the fluorescence intensities (open boxes) were measured by spectrofluorometry.

Construction of a bacterial gfp biosensor for trivalent arsenicals. A two-plasmid biosensor was constructed that utilizes the AfarsR gene under control of the arabinose promoter in one plasmid, pBADarsR (FIG. 3A), and the *A. ferrooxidans* ars operon promoter (p) controlling expression of gfp on a second plasmid, pACYC184-parsO-gfp (FIG. 3B). Expression of genes from the era promoter in pBADarsR is regulated by AraC, the regulator of the arabinose operon (11). In the presence of glucose and the absence of arabinose, AraC is a negative regulator that represses expression of genes behind the ara promoter, in this case, of AfarsR, resulting in gfp expression (FIG. 3C). As the concentration of arabinose is increased, AraC becomes a positive regulatory protein that drives expression of AfarsR, and consequently expression of gfp from pACYC184-pars0-gfp is decreased (FIG. 30). To increase sensitivity, the arsenic-hypersensitive *E. coli* strain AW3110 (ars:cam), which is unable to extrude As(III) (5), was utilized as host for the plasmids. Expression of gfp was visibly constitutive when AfArsR was repressed by growth on glucose (FIGS. 3C and 4A) and could be quantified spectrofluorometry (FIG. 4B). When AfArsR was induced by addition of 0.2% arabinose, gfp was repressed, and the cells were not fluorescent. Addition of 20 uM sodium arsenite dissociated AfArsR from pars, derepressing gfp expression. The intensity was proportional to the concentration of the As(III) (FIG. 4), which makes it possible to accurately quantify the concentration of As(III) in environmental samples. The decrease in cellular fluorescence and growth at 40 pM As(III) or higher is due to the hypersensitivity of AW3110. However, this corresponds to over 500 ppb, higher than the amount of arsenic found in most environmental situations, which should not limit the utility of the biosensor.

Figure 6:
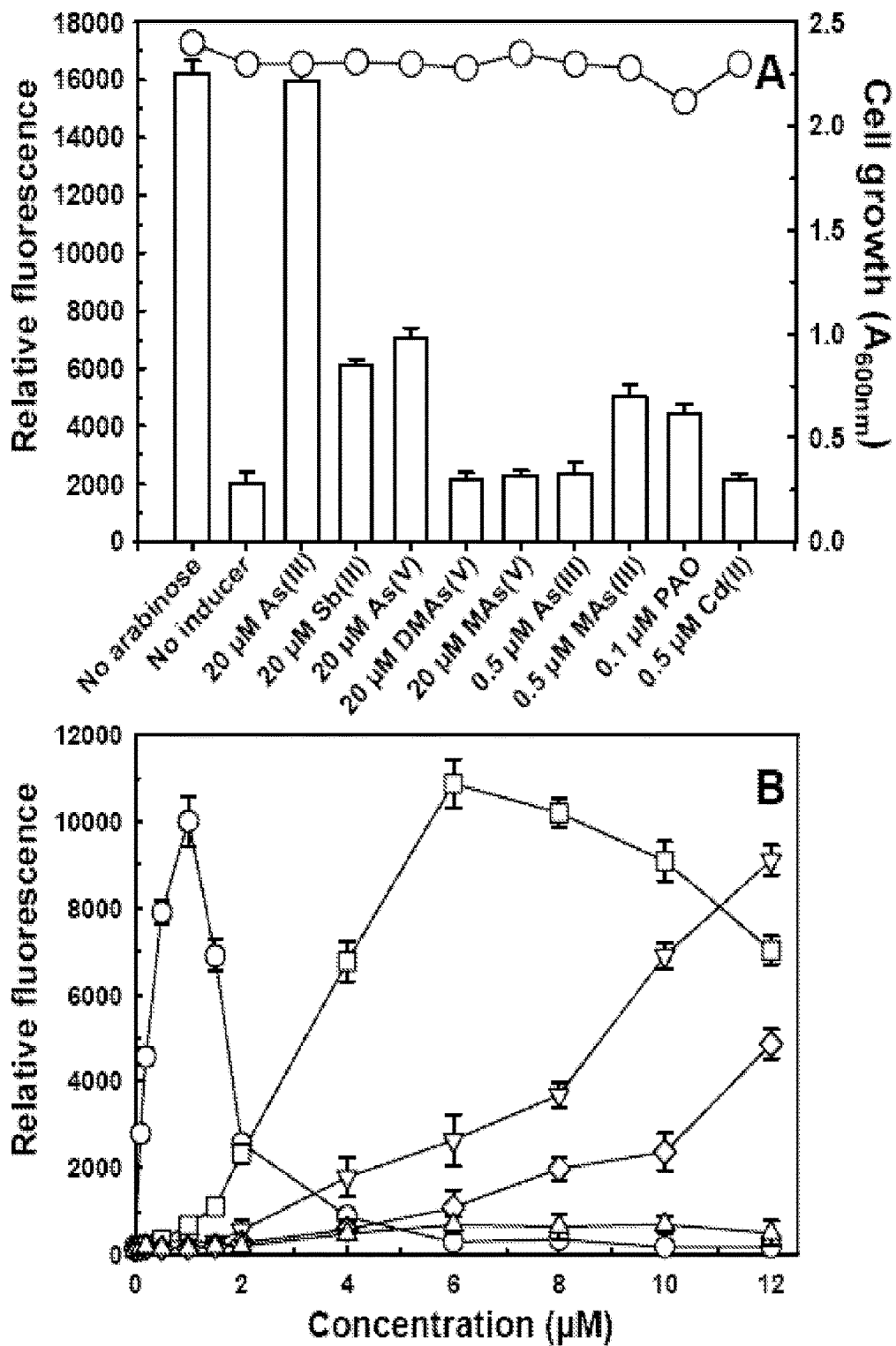
FIG. 6 shows the comparison of the response of the bacterial biosensor to inorganic and organic arsenicals. A) Cells were grown in LB medium in the absence of arabinose or with 0.2% arabinose and the indicated concentrations of inorganic arsenic. Cell growth (0) was monitored after 14 h incubation, the concentration of inducers was adjusted to prevent toxicity, and the fluorescence intensities (open boxes) were measured by spectrofluorometry. B) Cells were grown in LB medium with 0.2% arabinose and the indicated concentrations of inducers: (O), PAO; (□), MAs(IIII); (∇), As(III); (◇), Sb(III); (Δ), Cd(II).

Response of the biosensor to trivalent arsenicals. The in vivo response of the AfarsR-gfp biosensor to subtoxic concentrations of a variety of potential inducers was examined (FIG. 6A). PAO, MAs(Ill), As(III) and Sb(III) each induced gfp expression, while Cd(II), MAs(V) and DMAs (V) were not inducers. DMAs(III) was too unstable to test. The affinity of the biosensor for trivalent metalloids was quantified (FIG. 6B). Although each metalloid became toxic at higher concentrations, the apparent half maximal concentrations required for induction were approximately 0.25 $\mu$M for PAO, 3 $\mu$M for MAs(III), 10 $\mu$M for As(III). These results demonstrate that the AfarsR-gfp sensor is highly selective for aromatic and methylated trivalent arsenicals over inorganic arsenic in the order PAO>>MAs(III)>As(III).

Tuning the biosensor for sensitivity or selectivity. The data in FIG. 6 demonstrate the capability of the biosensor, but both the sensitivity and selectivity must be improved if it is to be useful under environmental conditions or to be able to detect specific species of arsenicals. We considered the possibility that, if AfArsR were produced in lower amounts, it should not repress gfp expression as tightly, allowing the sensor to respond to lower levels of arsenical inducer, leading to increased sensitivity. We also predicted that higher levels of ArsR would repress more tightly, so inducers with higher affinity would be required to derepress gfp expression, thus decreasing sensitivity but increasing selectivity.

Figure 7:
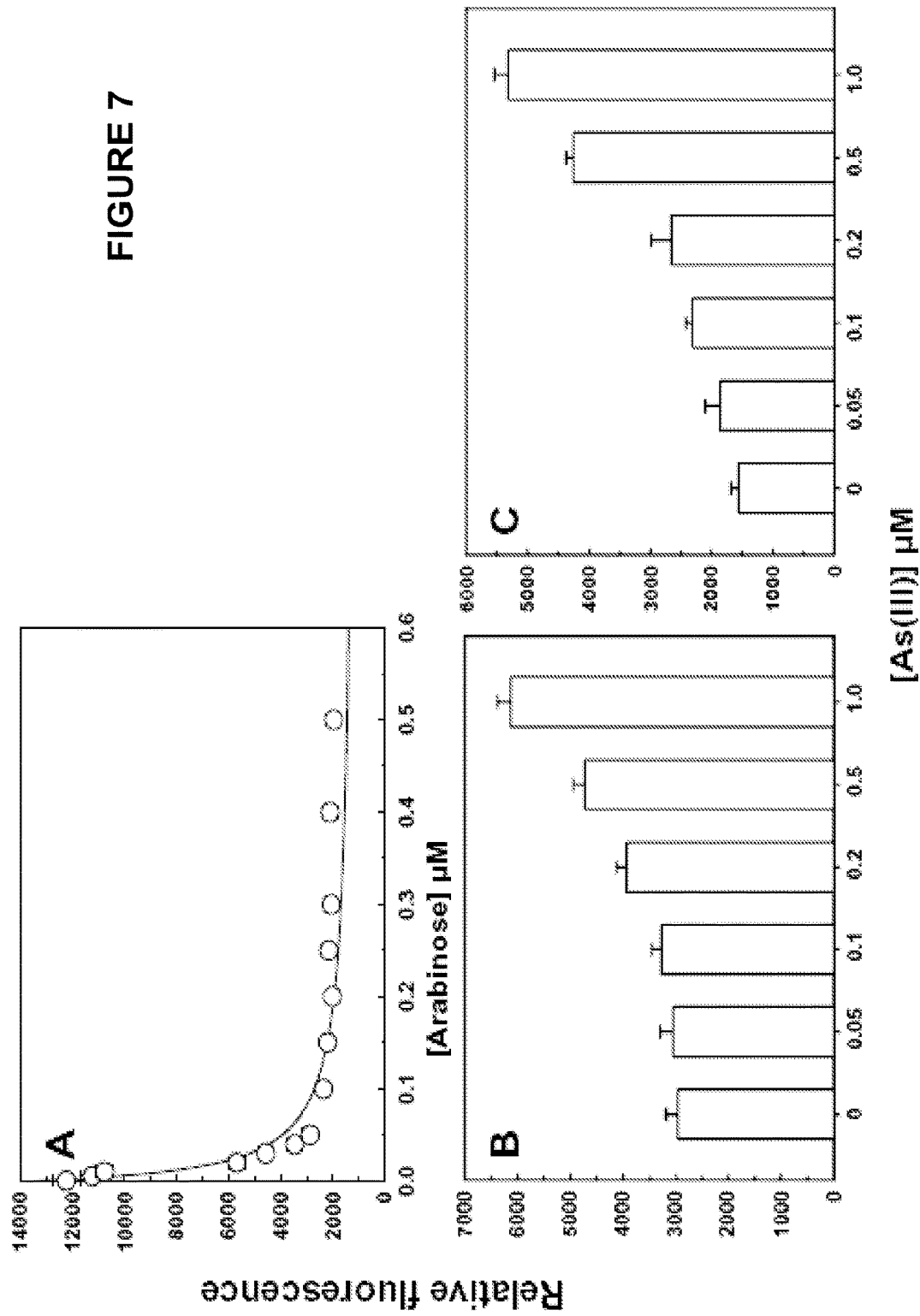
FIG. 7 shows optimizing the response to arabinose and increasing the sensitivity of the bacterial biosensor to inorganic As(III). A) To amplify the signal, the minimum concentration of arabinose required to repress gfp expression was determined. Cells were grown as described below with the indicated concentrations of arabinose in the absence of arsenical inducer. B) The sensitivity of the sensor to increasing As(III) concentration could be increased by lowering the arabinose concentration to B) 0.02% or C) 0.05%.

To explore these possibilities, conditions for variably regulating AfArsR levels were determined. Expression of AfarsR from the ara promoter in pBADarsR plasmid is regulated by AraC, the regulator of the arabinose operon. In the presence of glucose and the absence of arabinose, AraC is a negative regulator that represses expression of AfarsR, and lower levels of AfArsR facilitate gfp expression (FIG. 3C). As the concentration of arabinose is increased, AraC becomes a positive regulatory protein that drives expression of AfarsR, which consequently decreases expression of gfp from pACYC184-parsO-gfp (FIGS. 3C and 7A). Since arsenicals that bind to AfArsR would be expected to derepress gfp expression, the effect of inorganic As(III) concentration at several concentrations of arabinose was examined. At 0.02% arabinose repression, the sensitivity to low concentrations of inorganic arsenic was increased, but at the expense of a higher endogenous background level of gfp expression (FIG. 7B). At 0.05% arabinose the background was lower, but the level of induction was about the same (FIG. 7C).

When the effect of arsenical inducers was examined at 0.05% arabinose, the response was nearly linear with inorganic As(III), MAs(III) and PAO over the range of 0.1 to 0.5 I.JM (FIG. 8A). The signal with PAO was much greater than with the other two, and there was little discrimination between MAs(III) and As(III). Thus, at low arabinose, the biosensor is highly selective for PAO. To increase selectivity for MAs(III) over As(IIII), the concentration of arabinose was increased to 0.5% (FIG. 8B). With this level of arabinose, the response to inorganic arsenic was decreased, but the selectivity was increased. The signal with PAO was lost due to the toxicity of the phenyl derivative, but the response to MAs(III) was nearly linear over the range of 2-8 $\mu$M, with practically no response to inorganic As(III). Thus, at the higher level of arabinose, the biosensor becomes selective for MAs(III).

Figure 9:
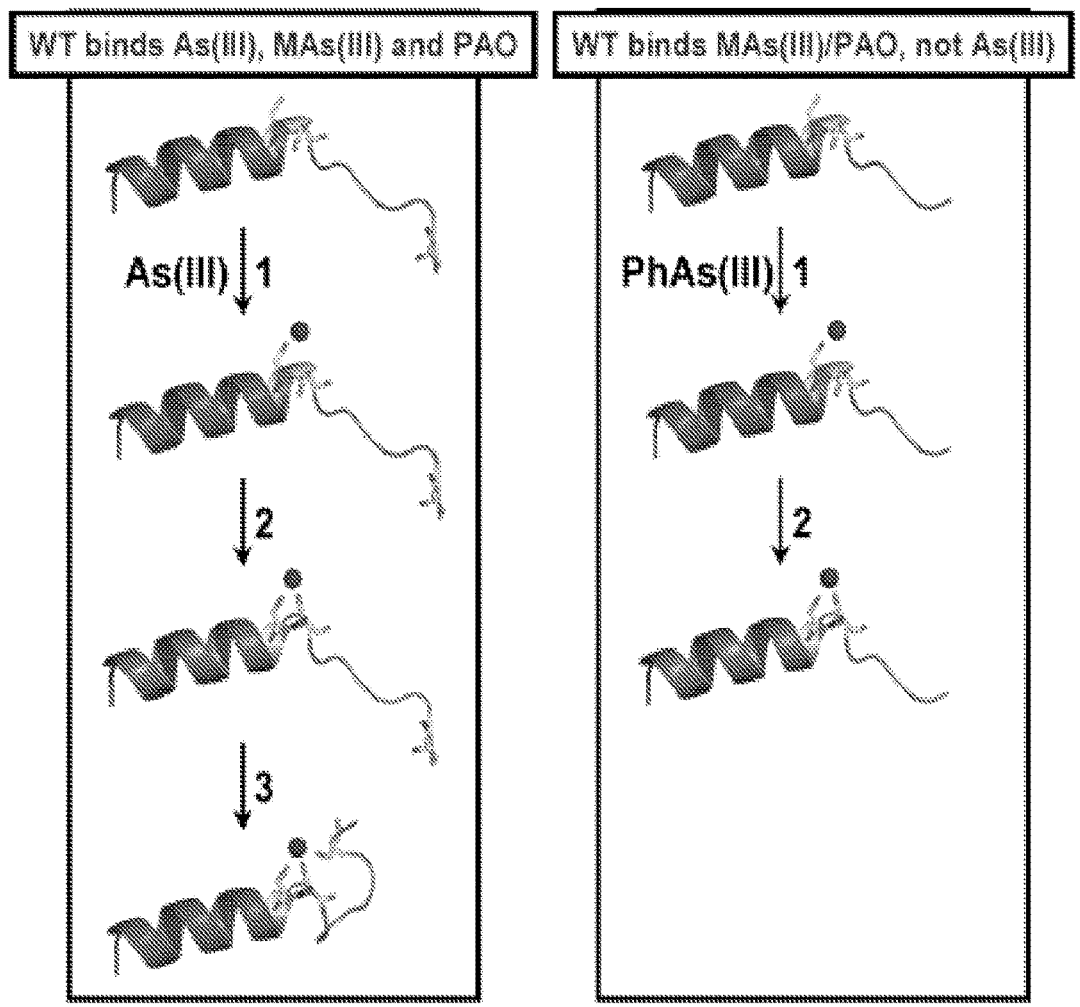
FIG. 9 shows the elimination of Cys102 from AfArsR protein and the resulting lack of binding of trivalent inorganic arsenic.
Figure 10:
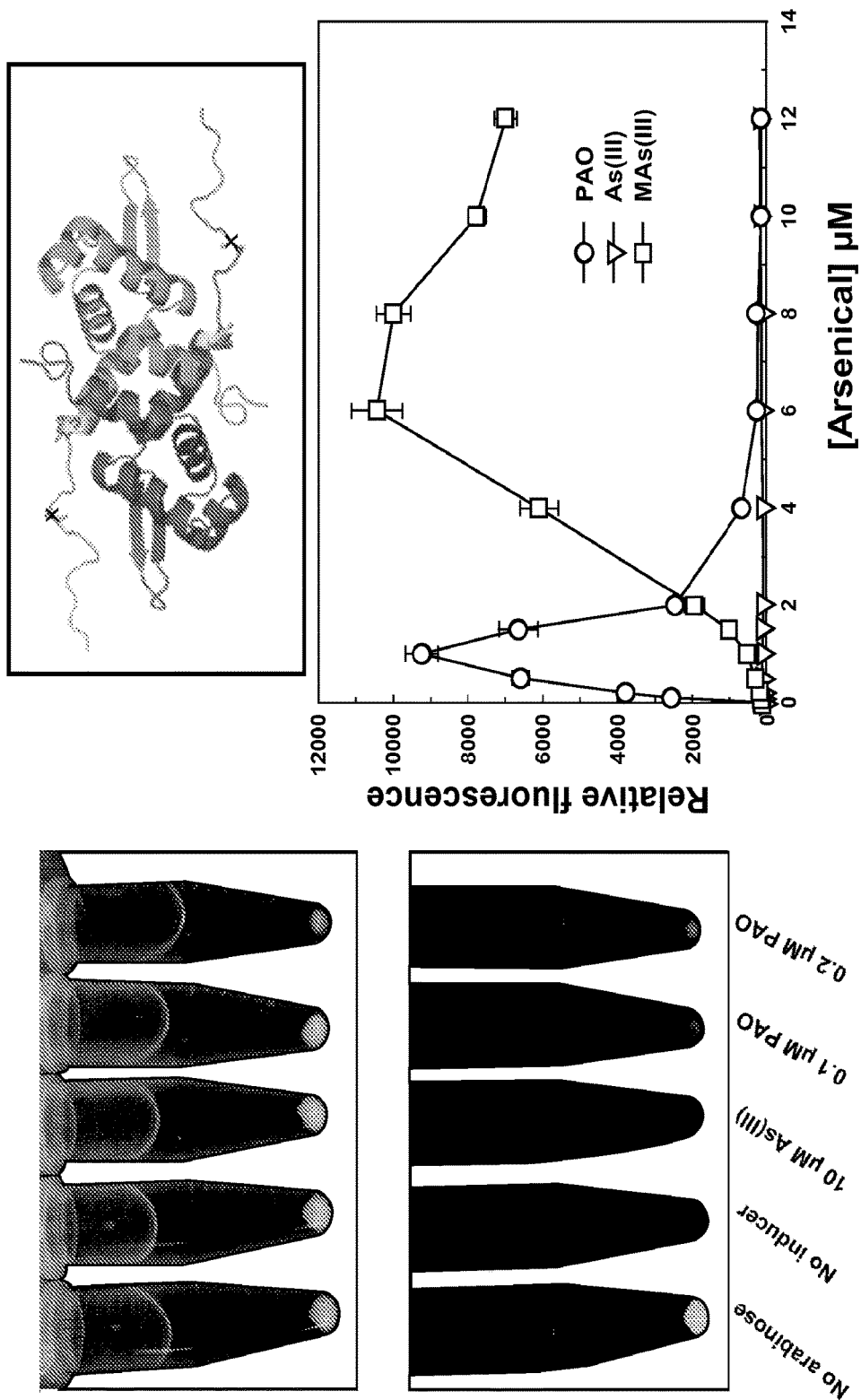
FIG. 10 shows the Cys102 lacking AfArsR biosensor and its resulting fluorescence in the presence of PAO, MAs(III), and inorganic As(III).

To make the biosensor specific for organic arsenicals, Cys102 was eliminated by mutation (FIG. 9). The resulting cellular biosensor still exhibited fluorescence in the presence of PAO but not in the presence of As(III) (FIG. 10, left). When quantified, there was no response to as much as 12 $\mu$M inorganic As(III) but sensed MAs(III) and PAO with high levels of fluorescence (FIG. 10, right).

AfArsR C102S responds in vitro selectively to trivalent organoarsenicals. The original cell-based biosensor exhibited high selectivity to organic over inorganic trivalent arsenicals (PhAs(III)>>Rox(III)>MAs(III)>As(III)). Although it could sense nanomolar concentrations of aromatic arsenicals, it still responded to micromolar concentrations of inorganic As(III). The basis of sensing is the binding of trivalent arsenic to three cysteine residues in AfArsR, Cys95, Cys96 and Cys102, which releases the repressor from ars operator/promoter DNA (FIG. 9). It was previously observed that substitution of Cys102 with a serine residue reduced affinity for As(III) by nearly an order of magnitude without affecting binding to DNA. From the results of x-ray absorption spectroscopy, high affinity binding to wild type AfArsR involved three sulfur ligands (FIG. 9), while only two-coordinate binding was observed with the C102S derivative (FIG. 9). Since binding of MAs(III), PhAs(III) or Rox(III) would be expected to require only two sulfur ligands, the possibility was considered that a biosensor with C102S AfArsR would respond to trivalent organoarsenicals with about the same affinity as wild type AfArsR. If so, the mutant could form the basis of a highly selective organoarsenic biosensor.

Binding of wild type AfArsR to DNA and dissociation upon binding of arsenicals was assayed by fluorescence anisotropy. In this assay, when AfArsR binds to fluorescein-labeled ars operator/promoter DNA, the rotation of the larger protein-DNA complex is slower than the rotation of free DNA, producing an increase in anisotropy. Anisotropy increased as a function of the concentration of wild type AfArsR, with a $K_d$ value of 0.9 $\mu$M (FIG. 2A). The effects of addition of As(III), MAs(V), MAs(III), PhAs(III), and Rox(III) on dissociation of wild type AfArsR were compared (FIGS. 11A and B). There was no effect of MAs(V) (FIG. 11A, curve 1) (or inorganic As(V); data not shown) on anisotropy of the wild type AfArsR-DNA complex. MAs (III) decreased anisotropy with a half-maximal concentration of approximately 2.5 $\mu$M (FIG. 11A, curve 3), while approximately 10 $\mu$M As(III) (FIG. 11B, curve 2) was required, a four-fold difference in affinity. PhAs(III) and Rox(III) decreased anisotropy with a half-maximal concentration of approximately 0.3 $\mu$M for each (FIG. 11A, curves 4 and 5). These results demonstrate that the PhAs(III), Rox(III) or MAs(III) bind to AfArsR and effect dissociation from DNA in the order PhAs(III)>>Rox(III)>MAs(III)>As(III).

The binding properties of the C102S derivative were examined (FIGS. 11C and D). In contrast to wild type AfArsR, C102S exhibited little response to As(III) up to 40 $\mu$M (FIG. 11C, curve 2 and D, curve 2). The response to MAs(III), Rox(III) and PhAs(III) was slightly higher than the wild type but still in the sub-micromolar range (FIG. 11C, curves 4 and 5, compared with FIG. 11A, curves 4 and 5). These results demonstrate that AfArsR could be engineered for increased selectivity for organoarsenicals by substitution of Cys102.

Figure 12A:
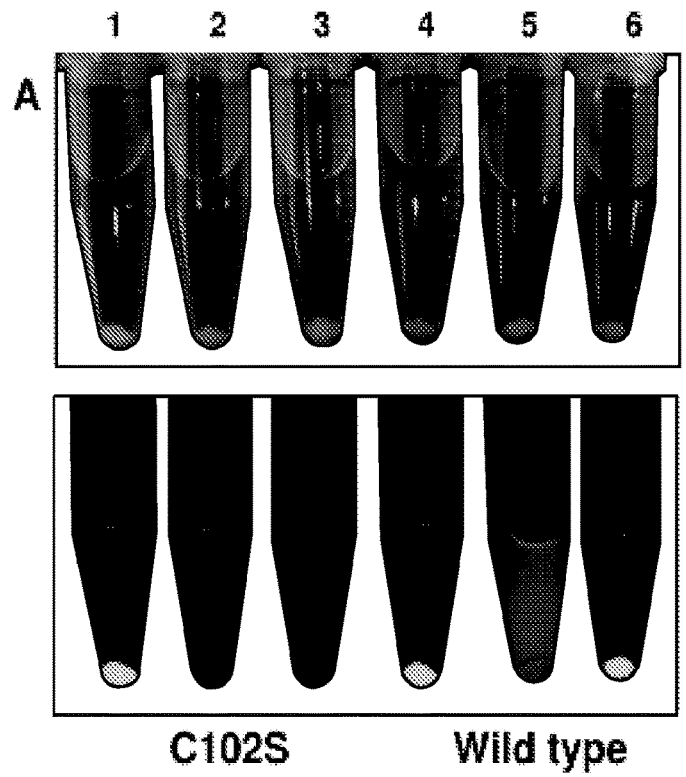
FIG. 12: Response of the bacterial biosensor with C102S mutant responded to As(III). Expression of the gfp reporter gene was assayed as described below. A) Effect of arabinose and As(III) on fluorescence of the biosensor cells under white light and UV light. Cells were grown in LB medium for 14 hr, centrifuged and visualized with a hand-held lamp under visible (up) or UV (down) light. 1) No arabinose; 2) 0.2% arabinose; 3) 0.2% arabinose+20 μM inorganic As(III). B. Fluorescence intensities were quantified by spectrofluorometry.
Figure 12B:
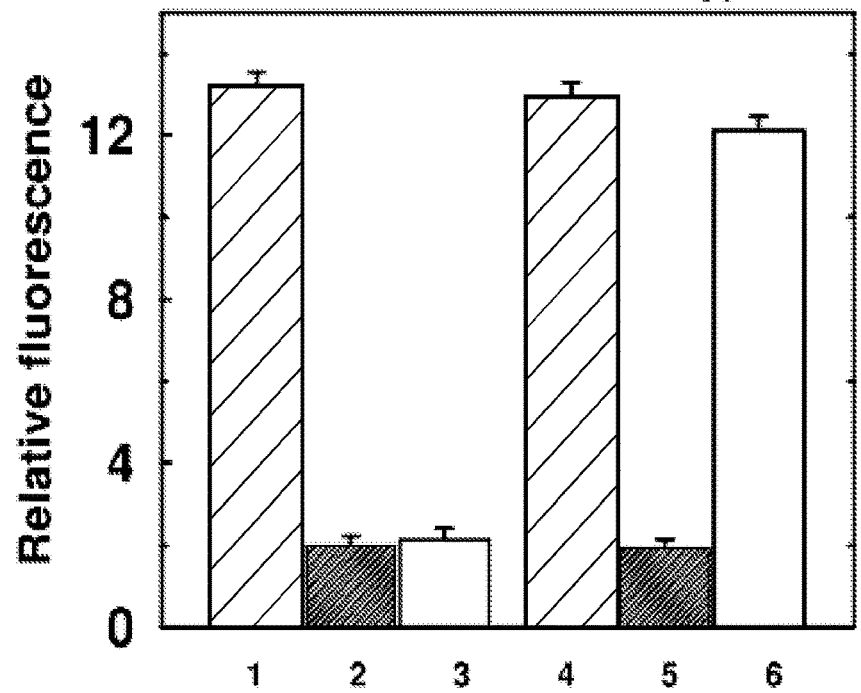

A C102S mutant biosensor loses the ability to respond to inorganic As(III). Since purified ArArsR C102S was shown to exhibit increased selectivity for trivalent organoarsenicals over inorganic As(III), a similar biosensor was constructed with the mutated gene for C102S. The biosensors incorporate either wild type or mutant afarsR gene under control of the arabinose promoter in one plasmid, pBADarsR, and the *A. ferrooxidans* ars operon promoter ($p_{ars}$) controlling expression of gfp on a second plasmid, pACYC188-parsO-gfp. Expression of genes from the ara promoter in pBADarsR is regulated by AraC, the regulator of the arabinose operon. In the presence of glucose and the absence of arabinose, AraC is a negative regulator that represses expression of genes behind the $p_{ara}$, in this case, of AfarsR, resulting in gfp expression. As the concentration of arabinose is increased, ArsC becomes a positive regulatory protein that drives expression of AfarsR, and consequently expression of gfp from pACYC188-parsO-gfp is decreased. To increase sensitivity, the arsenic-hypersensitive *E. coli* strain AW3110 (ars:cam), which is unable to extrude As(III), was utilized as host for the plasmids. Expression of GFP was visibly constitutive when either mutant or wild type AfarsR was repressed by growth on glucose (FIG. 12A, lanes 1 and 4) and could be quantified spectrofluorometry (FIG. 12B, lanes 1 and 4). When the repressors were induced by addition of 0.2% arabinose, gfp was repressed, and the cells were not fluorescent (FIGS. 12A and B, lanes 2 and 4). The biosensor with wild type AfarsR exhibited derepressed gfp expression upon addition of 20 µM sodium arsenite (FIGS. 12A and B, lanes 6). In contrast, the biosensor with the C102S mutant was not responsive to addition of arsenite (FIGS. 12A and B, lanes 4).

The sensitivity of the bio sensor can be increased by lowering the AfArsR levels. When produced in lower amounts, wild type AfArsR does not repress gfp expression as tightly, allowing the sensor to respond to lower concentrations of arsenical inducer. To improve the sensitivity of mutant biosensor, conditions for regulating AfArsR synthesis were examined (FIG. 13). As the concentration of arabinose is increased, AraC becomes a positive regulatory protein that drives expression of AfarsR, which consequently decreases expression of gfp from pACYC188-parsO-gfp. Wild type and mutant AfarsR exhibited similar repression by increasing concentrations of arabinose, with 0.05% sufficient for maximal repression (FIG. 13A). At 0.05% arabinose, the in vivo response of the mutant biosensor was examined at subtoxic concentrations of a trivalent arsenicals (FIG. 13B). Cellular gfp derepression by the trivalent organoarsenicals PhAs(III), Rox(III) and MAs(III) was proportional to the concentration of the inducer with both wild type and mutant repressor. Cells with either biosensor were unresponsive to MAs(V) and Rox(V). The difference between cells with the wild type and mutant repressor was that the wild type was induced by inorganic As(III) (FIG. 13B, lane 6) while the mutant did not respond to As(III) (FIG. 13B, lane 3). The response of the mutant biosensor to organoarsenicals was quantified (FIG. 13C). The apparent half maximal concentrations for induction were approximately 0.25 µM for PhAs(III) or Rox(III) and 3 µM for MAs(III). In the arsenic hypersensitive strain AW3110 the aromatic arsenicals became toxic at concentrations in excess of 2 µM, and MAs(III) was toxic at concentrations in excess of $10^{-5}$ M, which accounts for the decline in gfp expression at higher concentrations. Of significance, the mutant biosensor exhibited no response to As(III) even at $10^{-5}$ M (FIG. 13C). The response is visible to the eye under ultraviolet 264 light, which would allow the biosensor to be used in the field (FIG. 16A). These results demonstrate that the C102S biosensor is highly selective for trivalent aromatic and methylated arsenicals over inorganic arsenic in the order PhAs(III)>>Rox(III)>MAs(III)>>As(III).

Potential screening for MAs(V) and Rox(V) reducing microorganisms. Biotransformation between inorganic arsenicals and methylarsenicals was proved to be bidirectional. Noncarcinogenic MAs(V) is demethylated to more toxic and carcinogenic inorganic arsenic through microbial transformations. *Burkholderia* sp. MR1 was isolated and proved to reduce MAs(V) back to MAs(III). Based on this, the biosensor and *Burkholderia* were co-cultured with 2 µM MAs(V), phenylarsonic acid (PAA) and Rox(V) in M9 medium. After 8 hours incubation, the co-cultured cells only became responsive in the present of MAs(V). They didn't respond to PAA and Roxarsone (Rox(V)) (FIG. 14), but did respond to PAO and Rox(III). The results indicated that *Burkholderia* couldn't reduce these two substrates. The biosensor itself could neither reduce MAs(V) by itself nor detect MAs(V), but it could detect organic methyarsenicals by using a communal sequential reduction catalyzed by other soil microorganisms (FIG. 16B).

Figure 15:
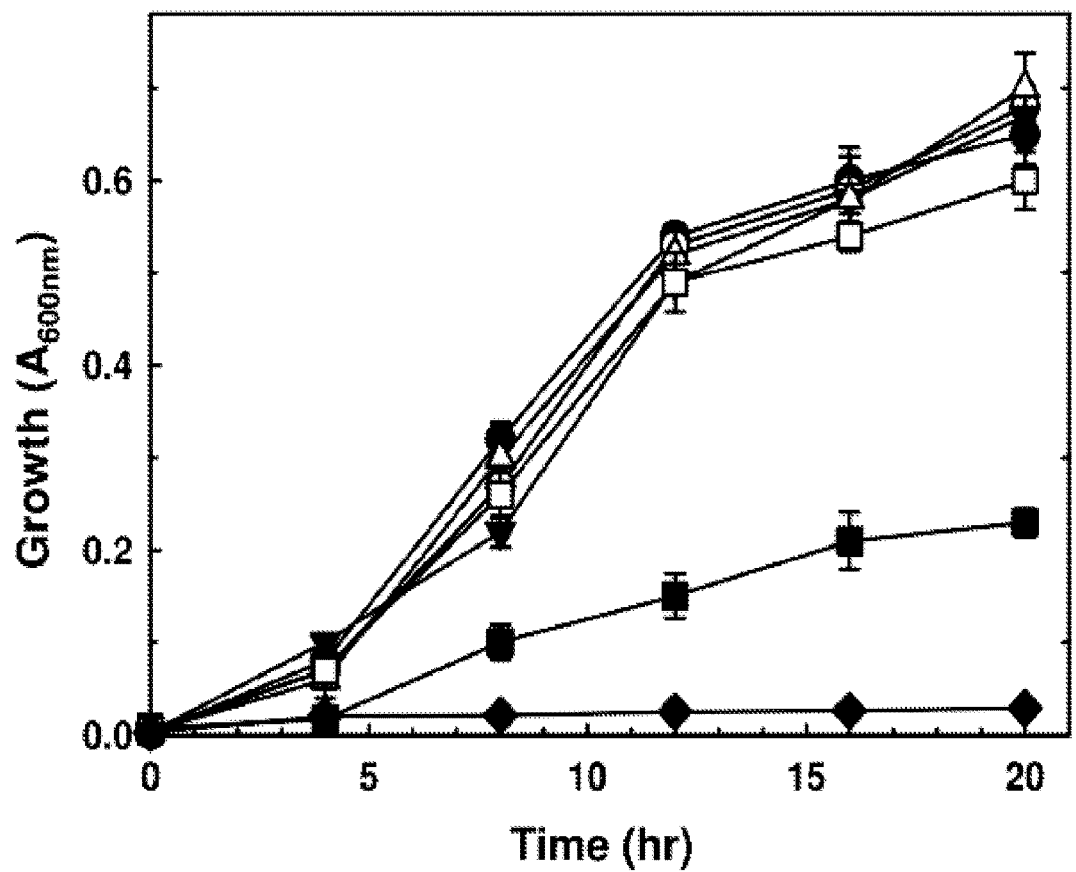
FIG. 15: Rox(III) is toxic. Rox(III) was more toxic compared to Rox(V). Cells were cultured at the indicated concentrations in M9 medium for overnight. (■), without arsenicals; (O), 0.2 μM Rox(V); (●), 0.2 μM Rox(III); ( ), 1 μM Rox(V); (▲) 1 μM Rox(III); ( ), 2 μM Rox(V); ( ), 2 μM Rox(III); Data are the mean±SE (n=3).

Rox(III) was proved to be much more toxic (FIG. 15). In this experiment, the biosensor didn't show fluorescent when co-cultured with *Burkholderia* in the present of Rox(V). It indicated that *Burkholderia* couldn't reduce Rox(V) to Rox(III). But it illustrates that this biosensor can be used for screening microorganisms that can reduce Rox(V) to Rox(III), an important step during the arsenic biogeocycle.

REFERENCES

1. Abernathy; et al. 2003. Health effects and risk assessment of arsenic. J Nutr 133:1536S-8S.
2. Agency, Environmental Protection. 2009. Organic arsenicals: product cancellation order and amendments to terminate uses. Federal Register 74:50187-50194.
3. Arao, et al. 2009. Uptake of aromatic arsenicals from soil contaminated with diphenylarsinic acid by rice. Environ Sci Technol 43:1097-101.
4. Bradford. 1976. A rapid and sensitive method for the quantitation of microgram quantities of protein utilizing the principle of protein-dye binding. Anal Biochem 72:248-54.
5. Carlin, et al. 1995. The ars operon of *Escherichia coli* confers arsenical and antimonial resistance. J Bacteriol 177:981-6.
6. Chang, et al. 1978. Construction and characterization of amplifiable multicopy DNA cloning vehicles derived from the P15A cryptic miniplasmid. J Bacteriol 134:1141-56.
7. Cortinas, et al. 2006. Anaerobic biotransformation of roxarsone and related N-substituted phenylarsonic acids. Environ Sci Technol 40:2951-7.
8. Edmonds, et al. 1987. Transformations of arsenic in the marine environment. Experientia 43:553-7.
9. Erickson. 2003. Field kits fail to provide accurate measure of arsenic in groundwater. Environ Sci Technol 37:35A-38A.
10. Gill, et al. 1989. Calculation of protein extinction coefficients from amino acid sequence data. Anal Biochem 182:319-326.

11. Guzman, et al. 1995. Tight regulation, modulation, and high-level expression by vectors containing the arabinose PBAD promoter. J Bacteriol 177:4121-30.
12. Kinniburgh, et al. 2002. Arsenic contamination in groundwater: some analytical considerations. Talanta 58:165-80.
13. Laemmli. 1970. Cleavage of structural proteins during the assembly of the head of bacteriophage T4. Nature 227:680-5.
14. Maejima, et al. 2011. Transformation of diphenylarsinic acid in agricultural soils. J Environ Qual 40:76-82.
15. Mukhopadhyay, et al. 2002. Arsenate reductases in prokaryotes and eukaryotes. Environ Health Perspect 110 Suppl 5:745-8.
16. Qin, et al. 2007. Convergent evolution of a new arsenic binding site in the ArsR/SmtB family of metalloregulators. J Biol Chem 282:34346-34355.
17. Qin, et al. 2009. Biotransformation of arsenic by a Yellowstone thermoacidophilic eukaryotic alga. Proc Natl Acad Sci USA 106:5213-7.
18. Qin, et al. 2006. Arsenic detoxification and evolution of trimethylarsine gas by a microbial arsenite S-adenosylmethionine methyltransferase. Proc Natl Acad Sci USA 103:2075-80.
19. Rahman et al. 2002. Effectiveness and reliability of arsenic field testing kits: are the million dollar screening projects effective or not? Environ Sci Technol 36:5385-94.
20. Ramanathan, et al. 1997. Sensing antimonite and arsenite at the subattomole level with genetically engineered bioluminescent bacteria. Anal Chem 69:3380-4.
21. Rensing, et al. 2009. Heavy metals cycles (arsenic, mercury, selenium, others), p. 205-219. In M. Schaechter (ed.), Encyclopedia of Microbiology. Elsevier, Oxford, U.K.
22. Ron. 2007. Biosensing environmental pollution. Curr Opin Biotechnol 18:252-6.
23. Sambrook, et al. 1989. Molecular cloning, a laboratory manual, vol. Cold Spring Harbor Laboratory, New York.
24. San Francisco, et al. 1990. Identification of the metalloregulatory element of the plasmid-encoded arsenical resistance operon. Nucleic Acids Res 18:619-24.
25. Scott, et al. 1997. Genetically engineered bacteria: electrochemical sensing systems for antimonite and arsenite. Anal Chem 69:16-20.
26. Shetty, et al. 2003. Luminescence-based whole-cell-sensing systems for cadmium and lead using genetically engineered bacteria. Anal Bioanal Chem 376:11-7.
27. Shi, et al. 1996. The role of arsenic-thiol interactions in metalloregulation of the ars operon. J Biol Chem 271:9291-7.
28. Stolz, et al. 2007. Biotransformation of 3-nitro-4-hydroxybenzene arsonic acid (roxarsone) and release of inorganic arsenic by *Clostridium* species. Environ Sci Technol 41:818-23.
29. Sun, et al. 2001. Role of cysteinyl residues in sensing Pb(II), Cd(II), and Zn(II) by the plasmid p1258 CadC repressor. J Biol Chem 276:14955-60.
30. Tchounwou, et al. 2004. Arsenic toxicity, mutagenesis, and carcinogenesis—a health risk assessment and management approach. Mol Cell Biochem 255:47-55.
31. Wu, et al. 1991. The ArsR protein is a trans-acting regulatory protein. Mol Microbiol 5:1331-6.
32. Xu, et al. 1996. The chromosomal arsR gene of *Escherichia coli* encodes a trans-acting metalloregulatory protein. J Biol Chem 271:2427-32.
33. Ye, et al. 2005. Crystal structure of the *Staphylococcus aureus* p1258 CadC Cd(II)/Pb(II)/Zn(II)-responsive repressor. J Bacteriol 187:4214-21.
34. Ye, et al. 2012. Arsenic biomethylation by photosynthetic organisms. Trends Plant Sci 17:155-62.
35. Yin, et al. 2011. Biotransformation and volatilization of arsenic by three photosynthetic cyanobacteria. Plant Physiol 156:1631-8.
36. Yoshinaga, et al. 2011. Demethylation of methylarsonic acid by a microbial community. Environ Microbiol 13:1205-15.
37. Zhou, et al. 2004. *Leishmania major* LmACR2 is a pentavalent antimony reductase that confers sensitivity to the drug Pentostam. J Biol Chem 279:37445-51.

What is claimed is:

1. A method of detecting trivalent organic arsenic in a sample comprising contacting the sample with a prokaryotic host cell comprising (1) an AfArsR (As(III)-responsive repressor) protein and (2) an AfArsR gene from *Acidithiobacillus ferrooxidans* and arsO-gfp gene (arsenical resistance operon promoter-green fluorescent protein gene), wherein the arsO promoter is from *Acidithiobacillus ferrooxidans*, wherein the AfArsR protein is selected from the group consisting of a wild type AfArsR protein encoded by the AfArsR gene from *Acidithiobacillus ferrooxidans* and an AfArsR protein mutant of the wild type AfArsR protein encoded by the AfArsR gene from *Acidithiobacillus ferrooxidans*, which lacks Cys102 residue present in the wild type protein, and wherein the cell produces green fluorescent protein (GFP) and fluoresces in the presence of the trivalent organic arsenic.

2. The method of claim 1, wherein the organic arsenic comprises phenylarsenite, trivalent roxarsone, methylarsenite, or combinations thereof.

3. The method of claim 1, wherein the prokaryotic host cell comprises an *Escherichia coli* strain AW3110.

4. The method of claim 1, further comprising contacting the prokaryotic host cell with (a) about 0.5% arabinose wherein the method detects methylarsenite at a concentration of 2 to 8 µM or (b) about 0.05% arabinose wherein the method detects phenylarsenite or trivalent roxarsone at a concentration of 0.1 to 0.5 µM.

5. The method of claim 1, wherein the AfArsR protein is the AfArsR protein mutant of the wild type AfArsR protein encoded by the AfArsR gene from *Acidithiobacillus ferrooxidans*, which lacks Cys102 residue present in the wild type protein.

6. A method of detecting trivalent organic arsenic in a sample comprising contacting the sample with a prokaryotic host cell comprising (1) a wild type AfArsR (As(III)-responsive repressor) protein encoded by an AfArsR gene from *Acidithiobacillus ferrooxidans* and (2) the AfArsR gene from *Acidithiobacillus ferrooxidans* and arsO-gfp gene (arsenical resistance operon promoter-green fluorescent protein gene) wherein (a) the sample has a concentration of organic arsenic in the form of methylarsenite of $10^{-6}$ M to $10^{-5}$ M, or in the form of phenylarsenite of $10^{-8}$ M to $10^{-6}$ M, or in the form of trivalent roxarsone of $10^{-8}$ M to $10^{-6}$ M; (b) the arsO promoter is from *Acidithiobacillus ferrooxidans*; and (c) the cell fluoresces in the presence of the organic arsenic.

7. A method of detecting trivalent organic arsenic in a sample comprising contacting the sample with an *Escherichia coli* cell of an AW3110 strain comprising (1) an AfArsR (As(III)-responsive repressor) protein and (2) an AfArsR gene from *Acidithiobacillus ferrooxidans* and arsO-gfp gene (arsenical resistance operon promoter-green fluorescent protein gene), wherein (a) the sample has a concentration of organic arsenic in the form of methylarsenite of $10^{-6}$ M to $10^{-5}$ M, or in the form of phenylarsenite of $10^{-8}$ M to $10^{-6}$ M, or in the form of trivalent roxarsone of $10^{-8}$ M to $10^{-6}$ M; (b) the arsO promoter is from *Acidithiobacillus ferrooxidans*; (c) the AfArsR protein is a mutant of a wild type AfArsR protein encoded by the AfArsR gene from *Acidithiobacillus ferrooxidans*, which lacks Cys102 residue present in the wild type protein; and (d) the *Escherichia coli* cell fluoresces in the presence of the organic arsenic.

8. The method of claim 1, wherein the AfArsR protein is the wild type AfArsR protein encoded by the AfArsR gene from *Acidithiobacillus ferrooxidans*.

9. The method of claim 1, wherein the AfArsR protein is the AfArsR protein mutant, and the Cys102 residue of the wild type AfArsR protein is substituted with a serine residue.

10. The method of claim 2, wherein the organic arsenic comprises phenylarsenite at a concentration of $10^{-6}$ M to $10^{-5}$ M.

11. The method of claim 2, wherein the organic arsenic comprises methylarsenite at a concentration of $10^{-8}$ M to $10^{-6}$ M.

12. The method of claim 2, wherein the organic arsenic comprises trivalent roxarsone at a concentration of $10^{-8}$ M to $10^{-6}$ M.

* * * * *